United States Patent
Kim et al.

(10) Patent No.: US 10,533,992 B2
(45) Date of Patent: Jan. 14, 2020

(54) METHOD FOR SCREENING FOR SUNLIGHT PROTECTION FUNCTIONAL MATERIAL AND METHOD FOR EVALUATING SUNLIGHT PROTECTION EFFECT

(71) Applicant: AMOREPACIFIC CORPORATION, Seoul (KR)

(72) Inventors: Hyoung June Kim, Yongin-si (KR); Min Sik Choi, Yongin-si (KR); Ji Yong Jung, Yongin-si (KR); Ju Yearl Park, Yongin-si (KR); Tae Ryong Lee, Yongin-si (KR); Dong Wook Shin, Yongin-si (KR); Eui Dong Son, Yongin-si (KR); Min Jung Chae, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 149 days.

(21) Appl. No.: 15/559,348

(22) PCT Filed: Mar. 19, 2015

(86) PCT No.: PCT/KR2015/002659
§ 371 (c)(1),
(2) Date: Sep. 18, 2017

(87) PCT Pub. No.: WO2016/148324
PCT Pub. Date: Sep. 22, 2016

(65) Prior Publication Data
US 2018/0113121 A1    Apr. 26, 2018

(51) Int. Cl.
| | |
|---|---|
| *G01N 33/52* | (2006.01) |
| *G01N 33/53* | (2006.01) |
| *G01N 33/68* | (2006.01) |
| *G01N 33/50* | (2006.01) |
| *A61K 8/27* | (2006.01) |
| *A61K 8/29* | (2006.01) |
| *A61K 33/30* | (2006.01) |
| *A61K 33/00* | (2006.01) |
| *A61K 33/24* | (2019.01) |
| *A61K 8/37* | (2006.01) |
| *A61K 8/49* | (2006.01) |
| *A61Q 17/04* | (2006.01) |

(52) U.S. Cl.
CPC .............. *G01N 33/52* (2013.01); *A61K 8/27* (2013.01); *A61K 8/29* (2013.01); *A61K 8/37* (2013.01); *A61K 8/4966* (2013.01); *A61K 33/00* (2013.01); *A61K 33/24* (2013.01); *A61K 33/30* (2013.01); *A61Q 17/04* (2013.01); *G01N 33/5044* (2013.01); *G01N 33/53* (2013.01); *G01N 33/68* (2013.01); *G01N 33/6881* (2013.01); *G01N 2440/26* (2013.01)

(58) Field of Classification Search
None
See application file for complete search history.

(56) References Cited

U.S. PATENT DOCUMENTS

| | | | |
|---|---|---|---|
| 5,616,331 | A | 4/1997 | Allard et al. |
| 8,241,613 | B2 | 8/2012 | Candau et al. |
| 2002/0197633 | A1 | 12/2002 | Jones et al. |
| 2010/0172944 | A1 | 7/2010 | Laboureau et al. |
| 2013/0072572 | A1 | 3/2013 | Papazoglou et al. |
| 2013/0169951 | A1 | 7/2013 | Miura et al. |
| 2013/0324476 | A1 | 12/2013 | Delattre et al. |

FOREIGN PATENT DOCUMENTS

| | | |
|---|---|---|
| CN | 101336871 B | 11/2011 |
| JP | 2003-212745 A | 7/2003 |
| JP | 2010-155839 A | 7/2010 |
| JP | 2013-166132 A | 8/2013 |
| KR | 10-0151635 B1 | 10/1998 |
| KR | 10-2001-0065136 A | 7/2001 |
| KR | 10-2012-0059672 A | 6/2012 |
| KR | 10-2013-0037229 A | 4/2013 |

(Continued)

OTHER PUBLICATIONS

Wang et al. (Pharmaceuticals 2014 7: 545-594 134: 1083-1090 (Year: 2014).*
Gulson et al. (Toxicological Sciences 2010 115: 140-149) (Year: 2010).*
Glaser et al. (J. Allergy Clin Immunol 2009 123:1117-1123). (Year: 2009).*
Oplander et al. (Circ. Res. 2009 105:1031-1040). (Year: 2009).*
Remond et al. (J. Invest Dermatol 2014 134: 1083-1090). (Year: 2014).*

(Continued)

*Primary Examiner* — Changhwa J Cheu
(74) *Attorney, Agent, or Firm* — Merchant & Gould P.C.

(57) ABSTRACT

Unlike a conventional method for evaluating a degree of ultraviolet protection through visual evaluation, the disclosed method for measuring a sunlight protection function can accurately and objectively measure and determine a degree of sunlight protection by measuring a change due to a material to be measured with respect to an expression amount of skin tissue antimicrobial peptides (AMPs) in skin cells, which decrease from exposure to sunlight, and/or a generation amount of S-nitrosylated protein. Additionally, the disclosed measurement method can determine whether blue/violet light of wavelengths of 400-500 nm, which induces the most skin damage among visible rays, is blocked and provide a more specified sunlight protection effect evaluation result. Moreover, by using the disclosed measurement method, a degree of sunlight protection can be indexed, and a sunlight protection composition for protecting normal skin from the blue/violet light can be provided.

5 Claims, 37 Drawing Sheets

(56) References Cited

FOREIGN PATENT DOCUMENTS

KR 10-2015-0064579 A 6/2015

OTHER PUBLICATIONS

Office Action from corresponding Japanese Patent Application No. 2017-547424, dated Dec. 11, 2018.
Antal et al., "Impact of Vitamin D3 on Cutaneous Immunity and Antimicrobial Peptide Expression," Dermato-Endocrinology, 3(1):18-22 (2011).
International Search Report for PCT/KR2015/002659 (dated Dec. 30, 2015).
Written Opinion for PCT/KR2015/002659 (dated Dec. 30, 2015).
Office Action from corresponding Chinese Patent Application No. 201580080137.5, dated Feb. 18, 2019.
Office Action from corresponding Korean Patent Application No. 10-2013-0149433, dated Aug. 21, 2019.
Office Action from corresponding Korean Patent Application No. 10-2013-0149432, dated Sep. 4, 2019.
Glaser et al., "UV-B radiation induces the expression of antimicrobial peptides in human keratinocytes in vitro and in vivo", J Allergy Clin Immunol, vol. 123, No. 5, pp. 1117-1123 (May 2009).

\* cited by examiner

[FIG. 1A]
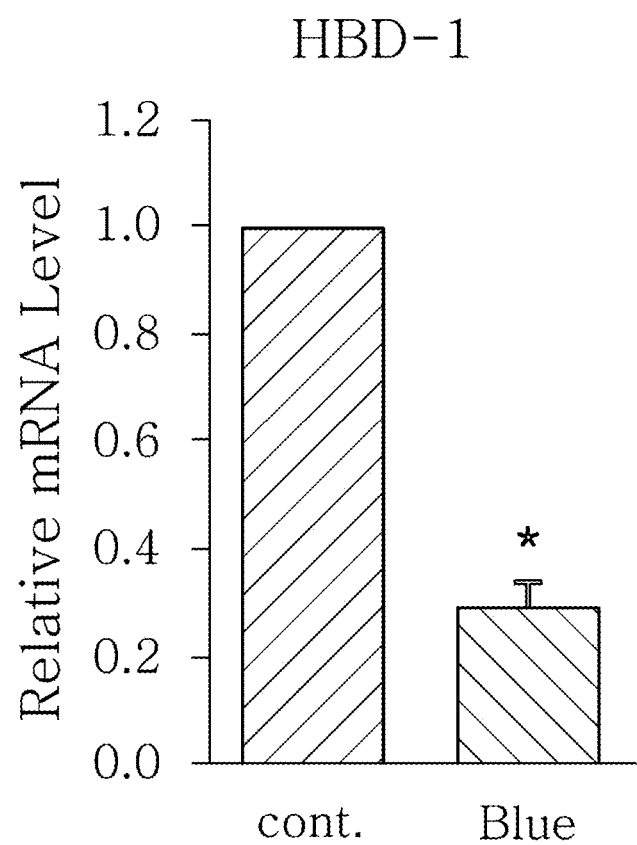

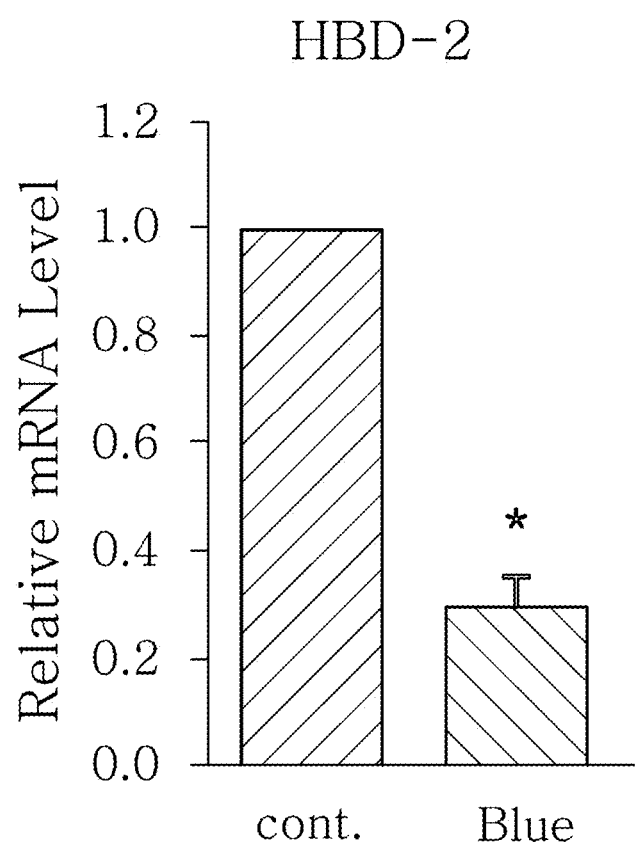
[FIG. 1B]

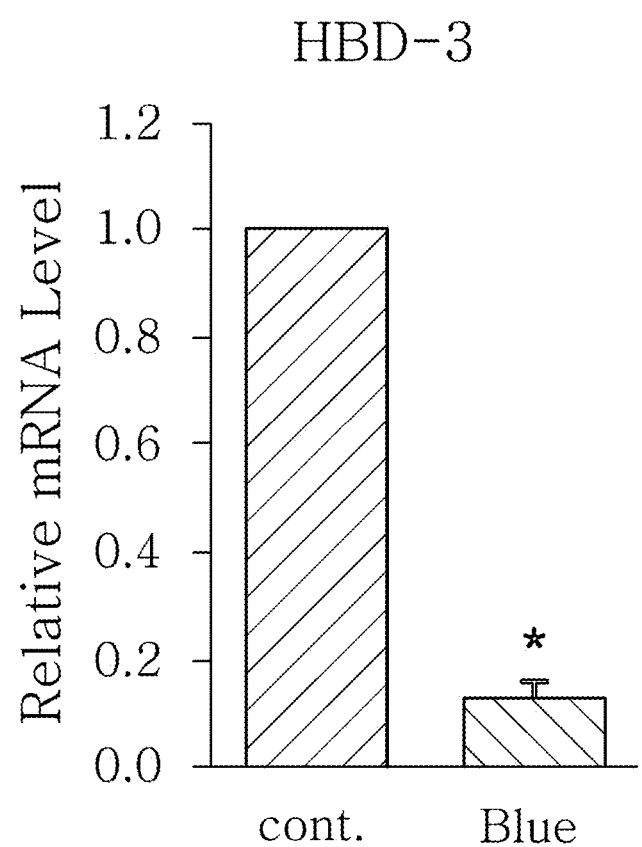
[FIG. 1C]

[FIG. 1D]
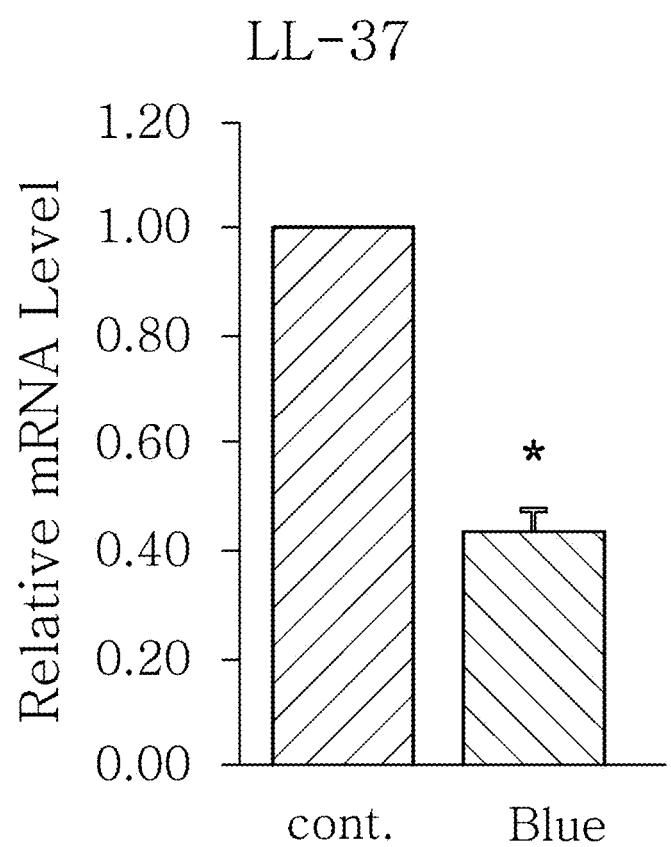

[FIG. 1E]
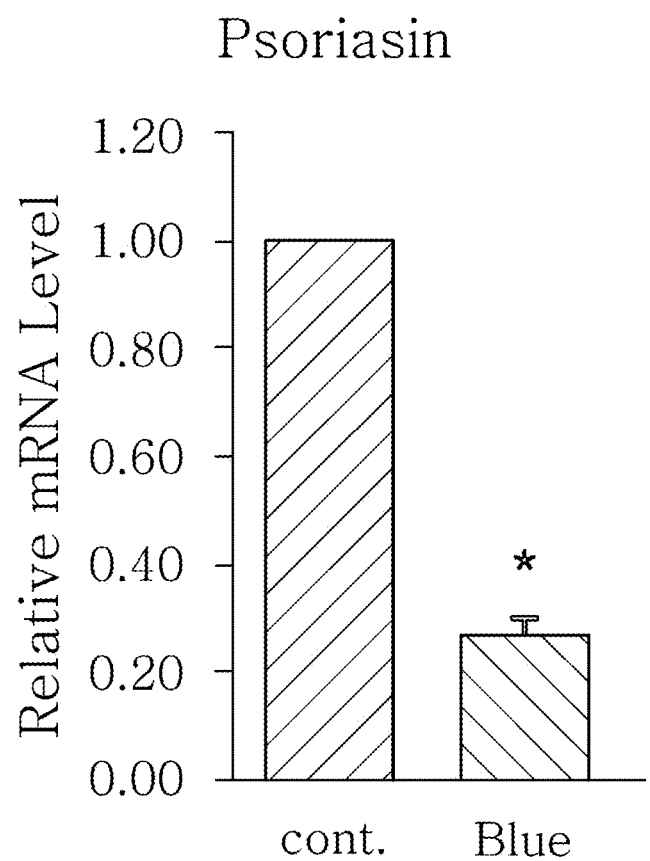

[FIG. 1F]
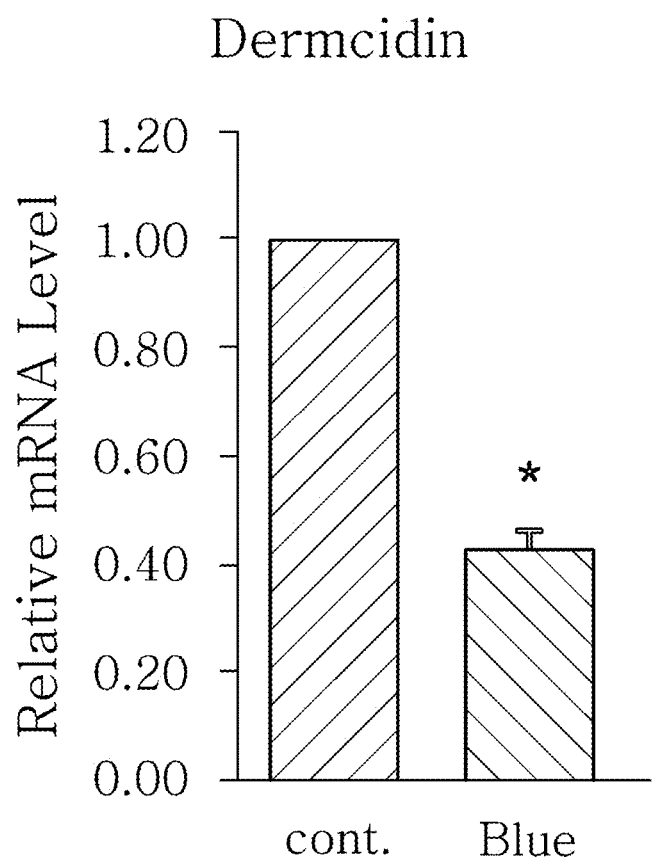

[FIG. 1G]
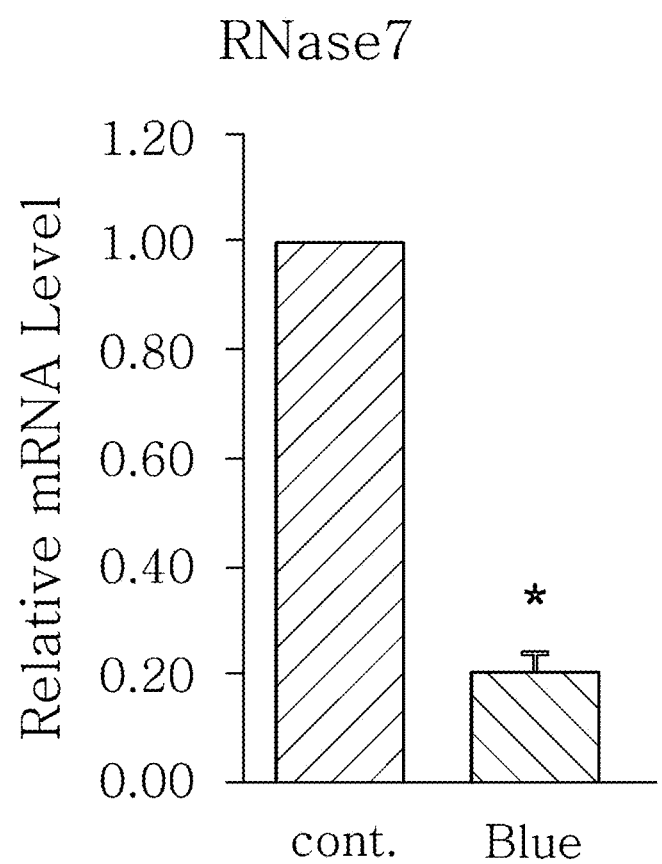

[FIG. 2A]
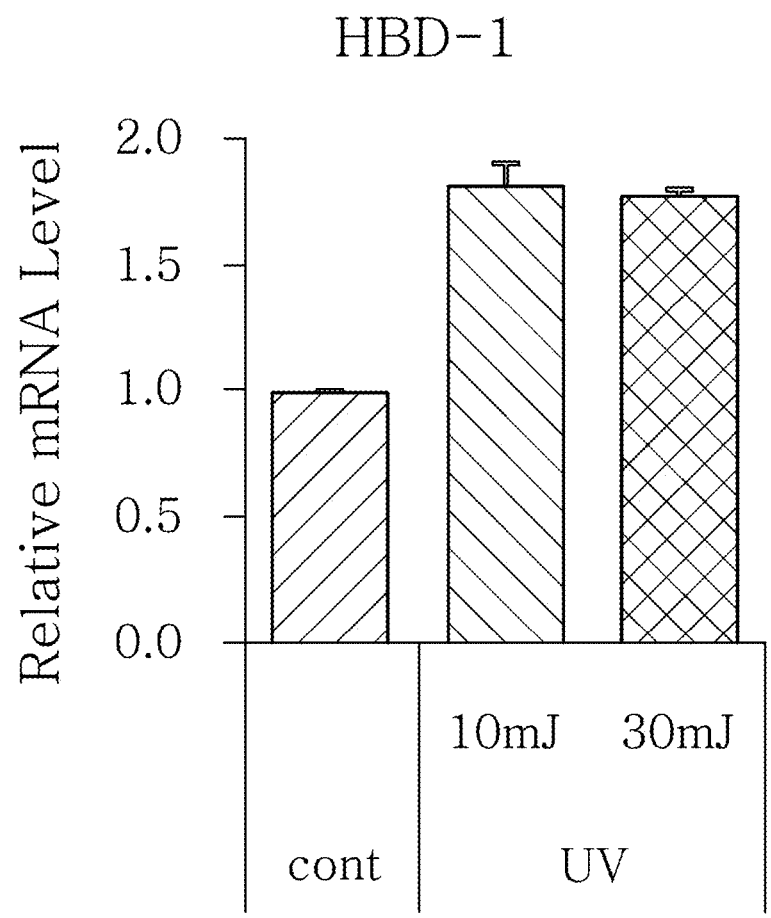

[FIG. 2B]
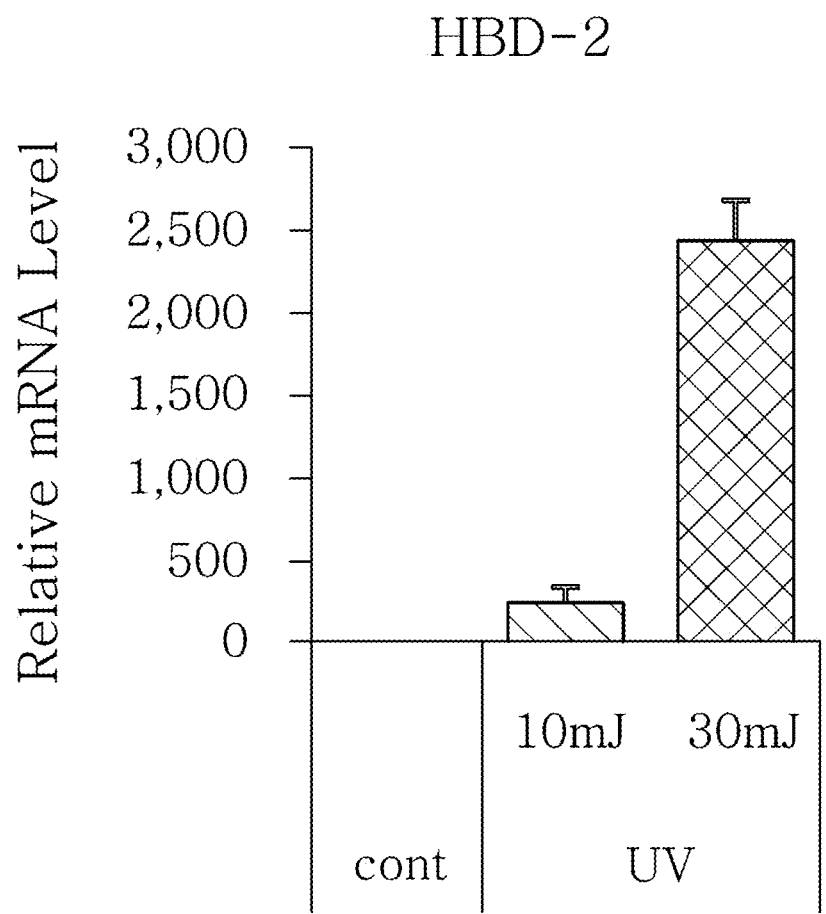

[FIG. 2C]
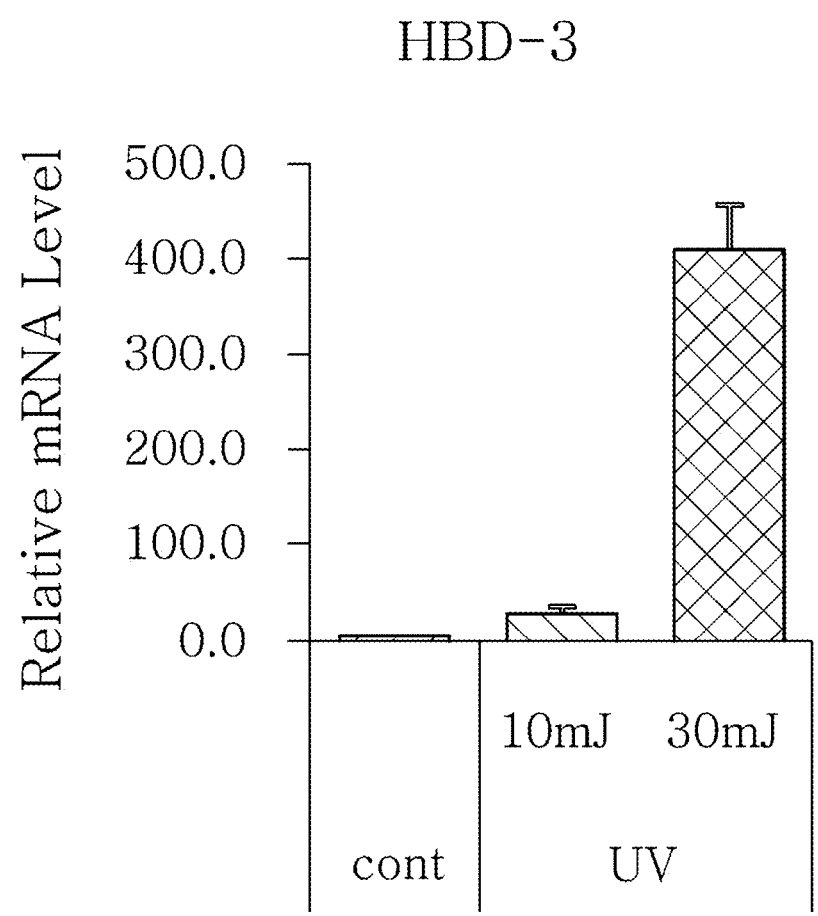

[FIG. 2D]
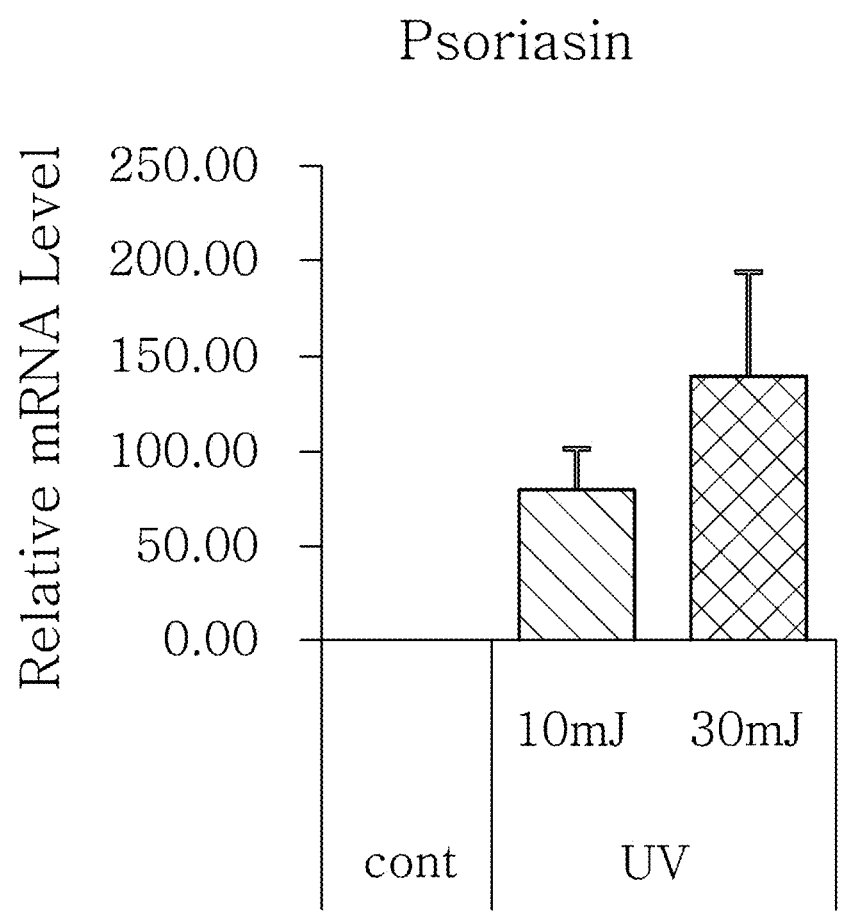

[FIG. 2E]
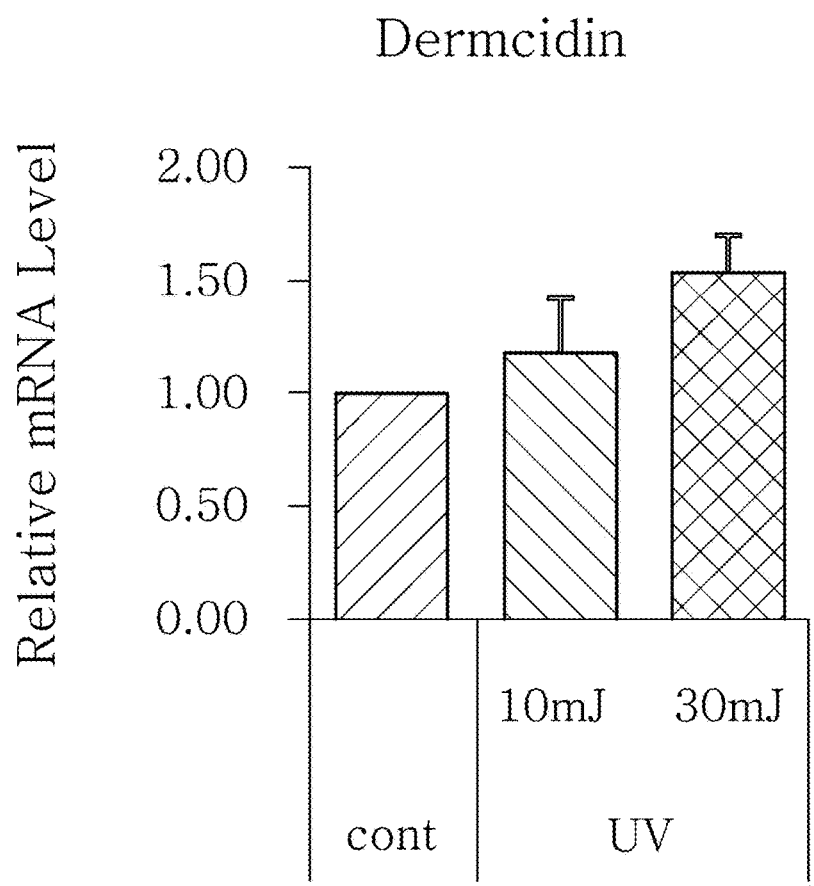

[FIG. 2F]
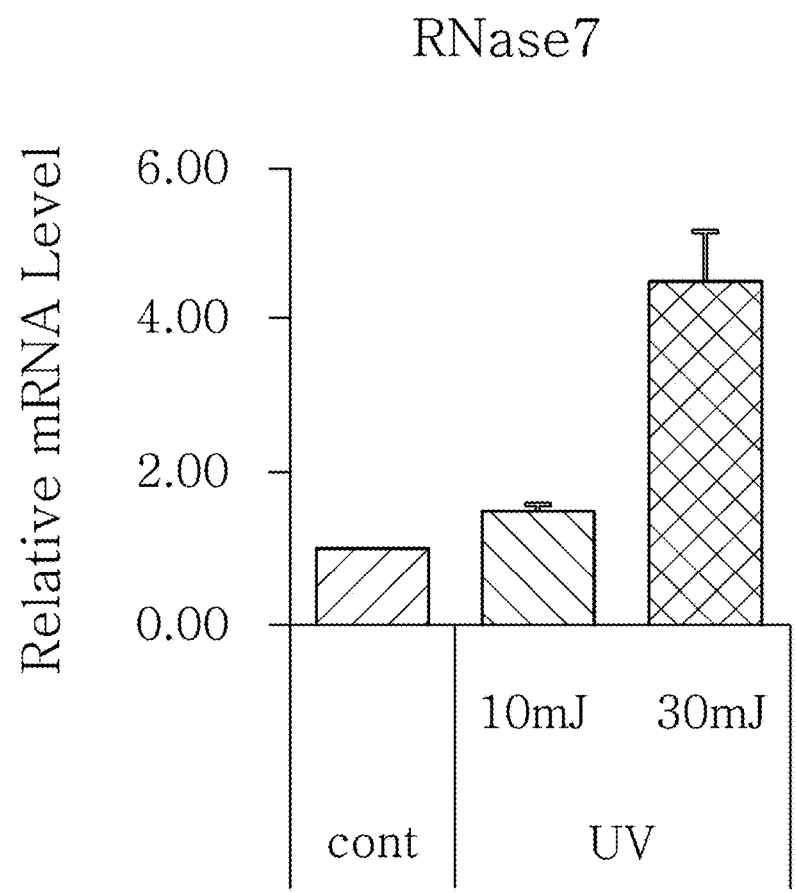

[FIG. 3A]
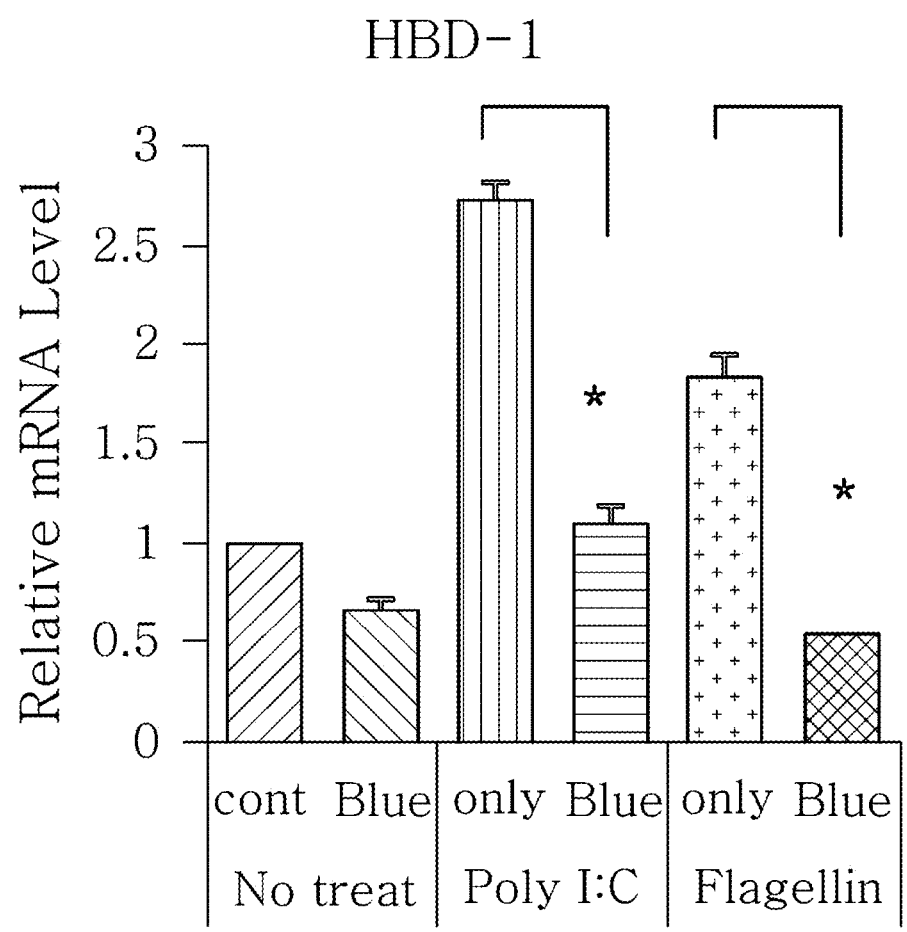

[FIG. 3B]
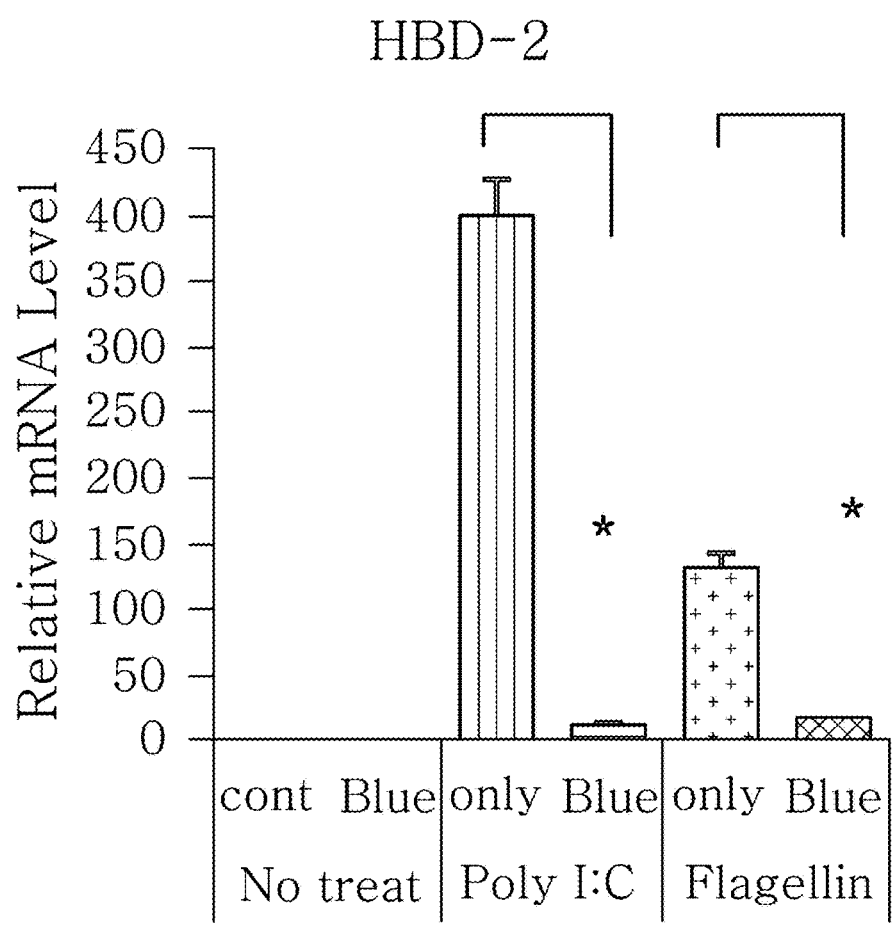

[FIG. 3C]
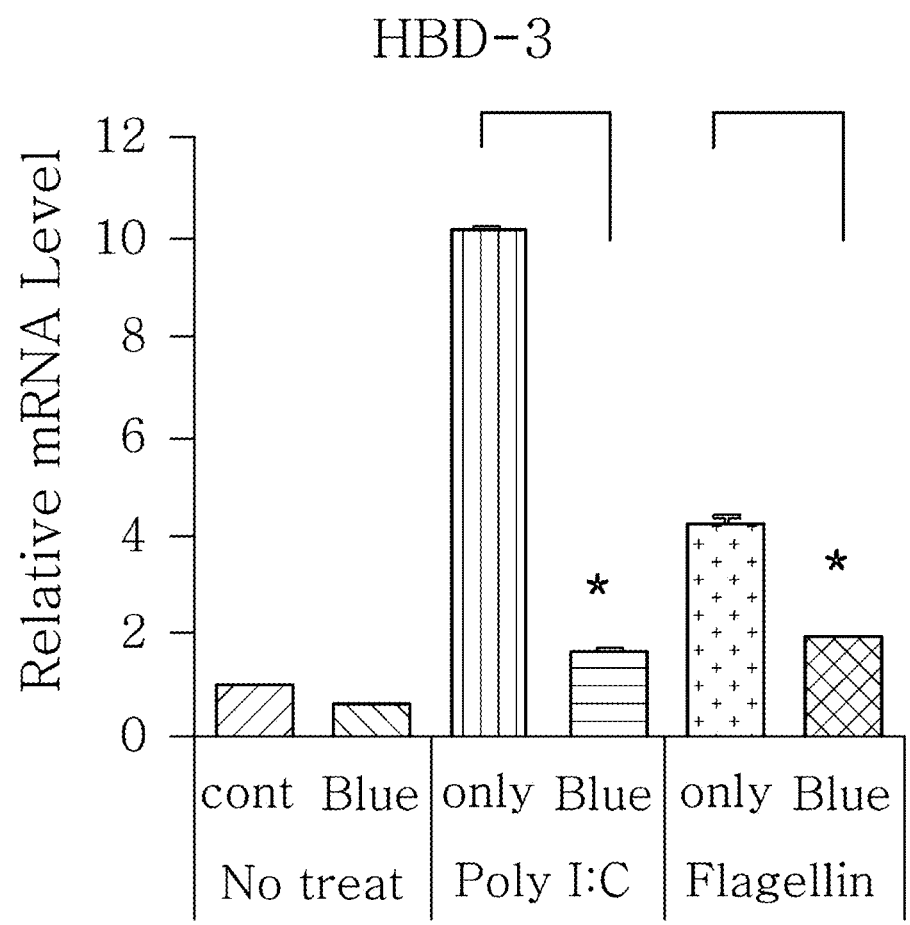

[FIG. 3D]
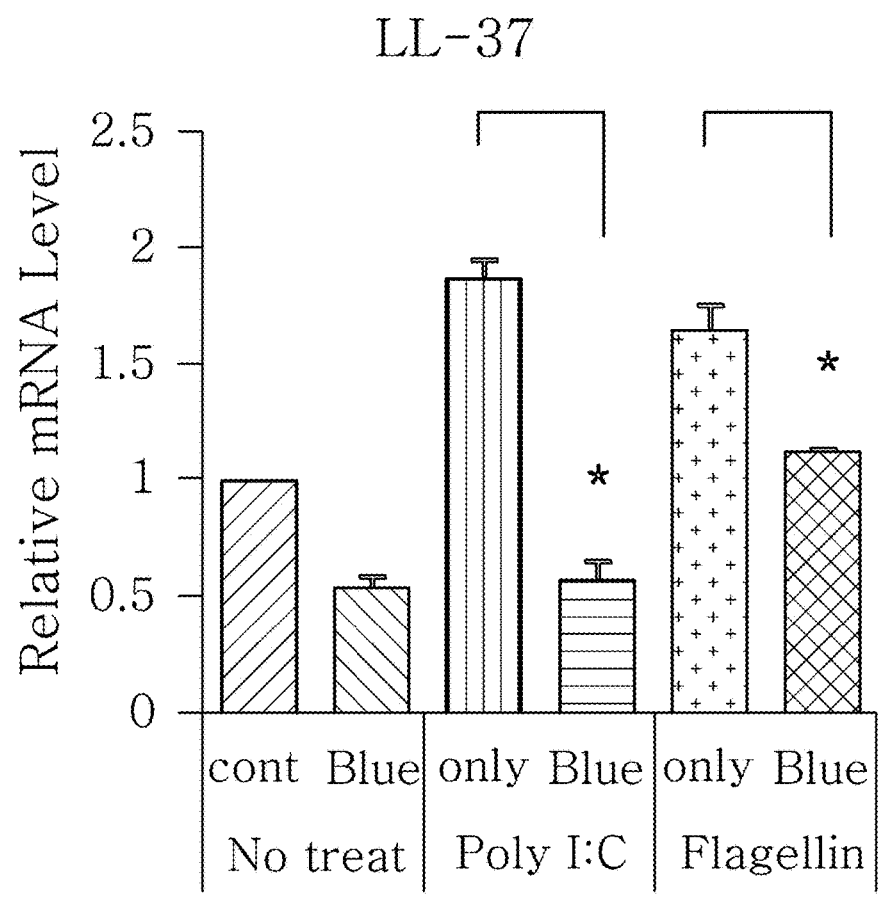

[FIG. 3E]
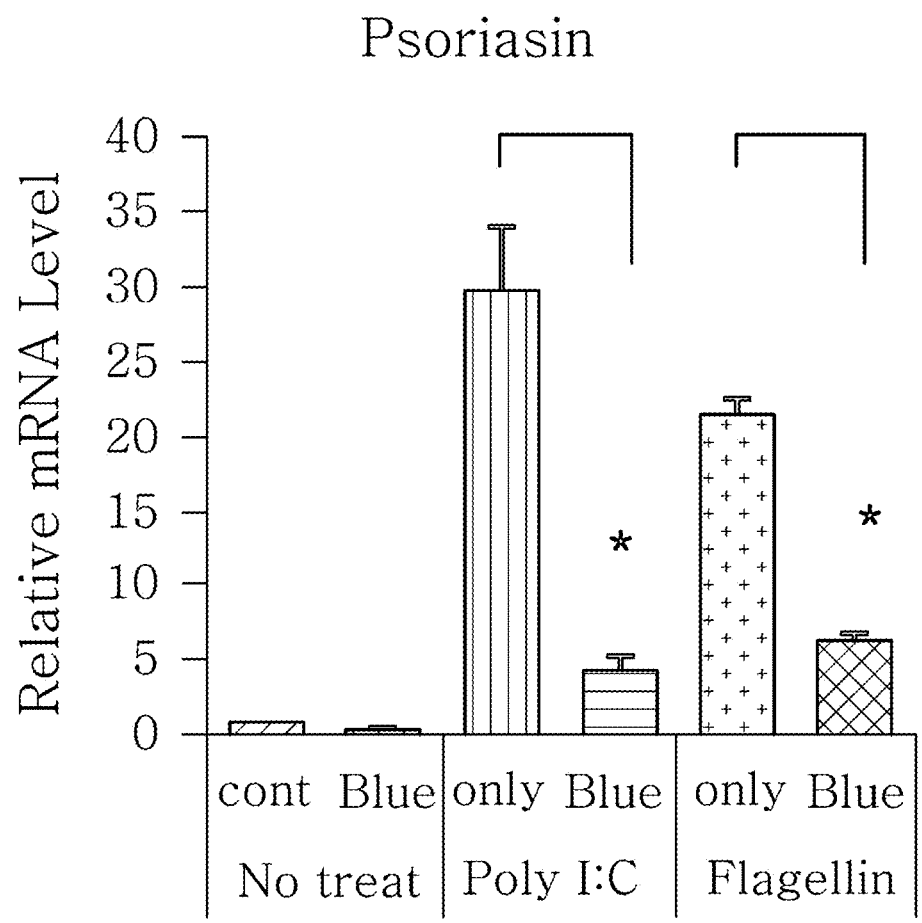

[FIG. 3F]
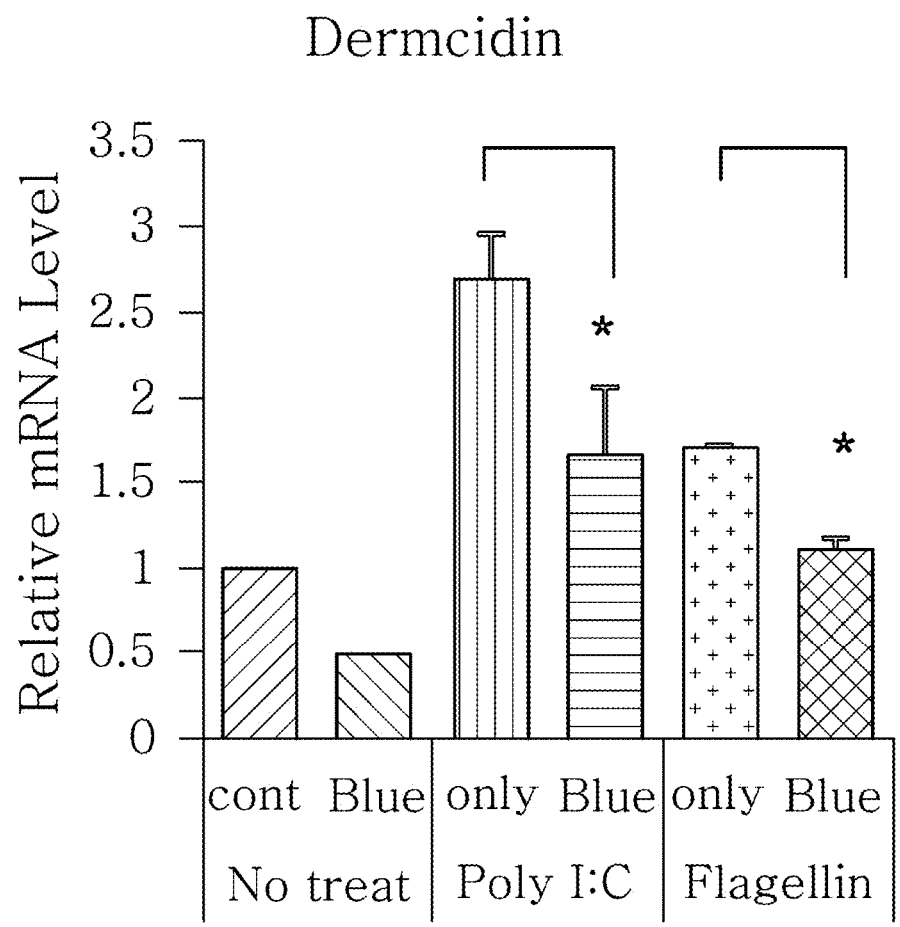

[FIG. 3G]
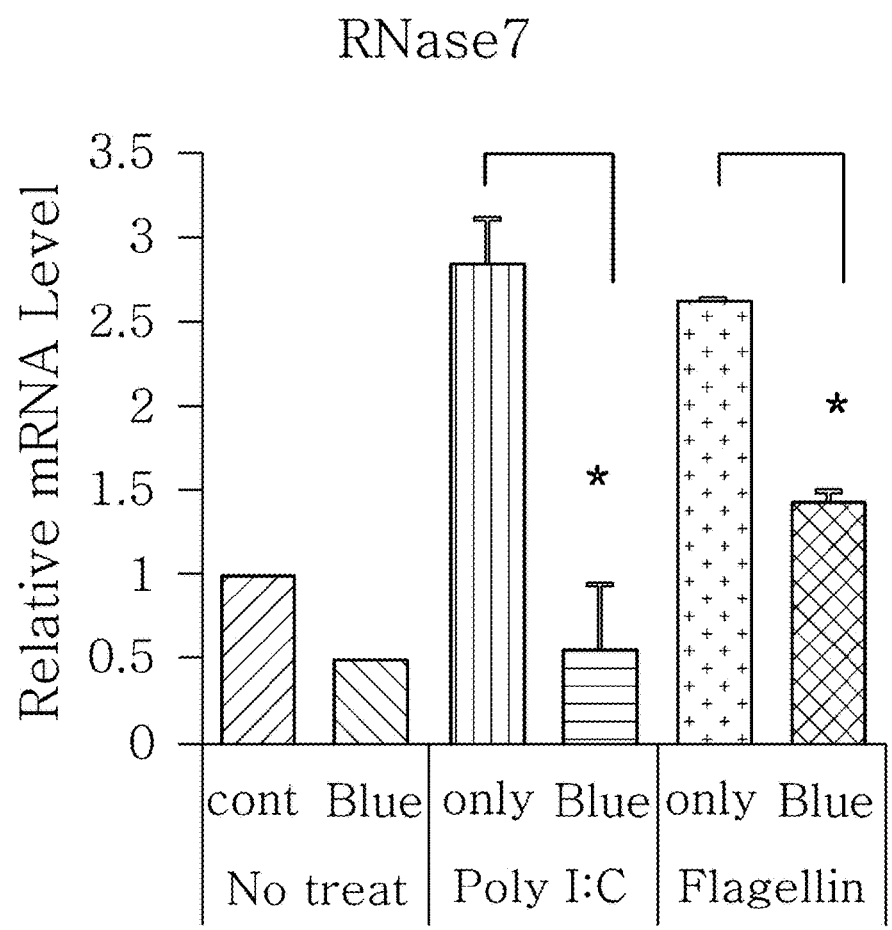

[FIG. 4A]
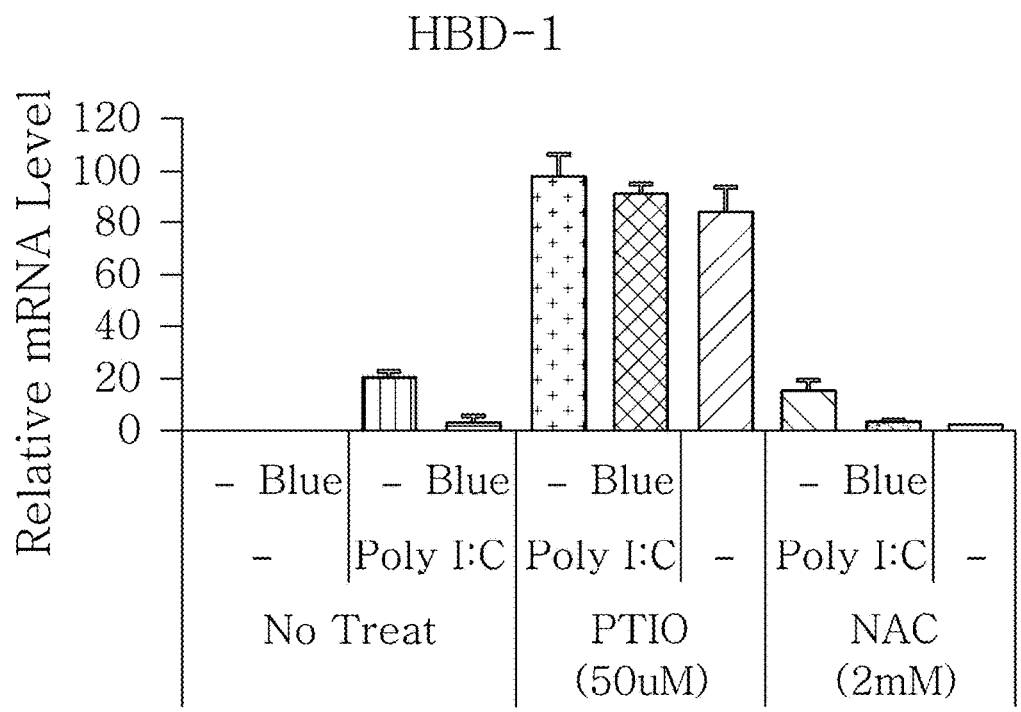

[FIG. 4B]
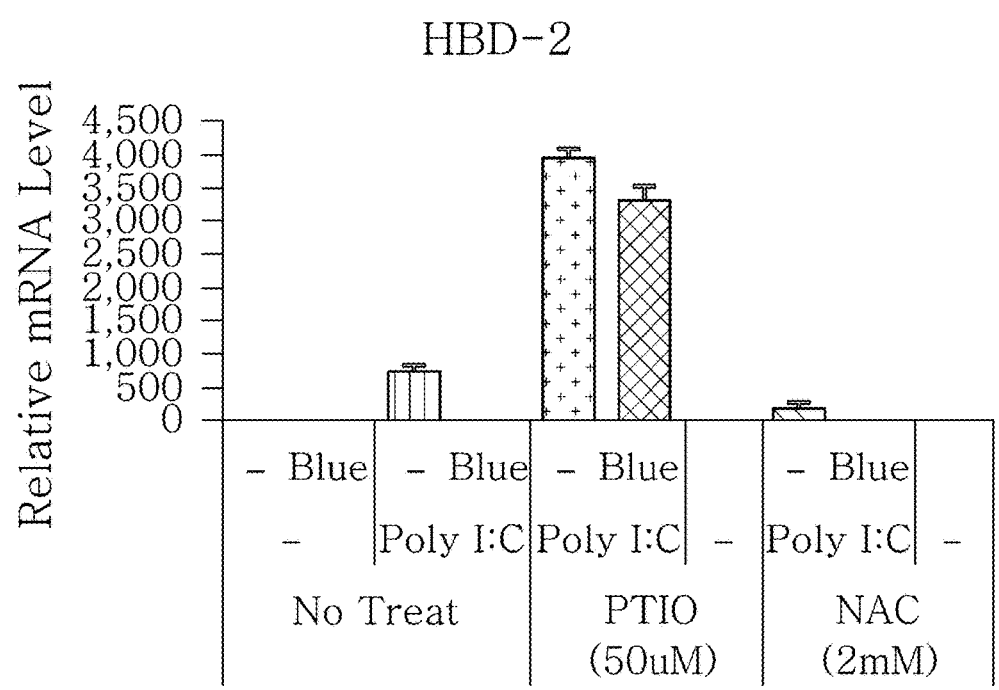

[FIG. 4C]
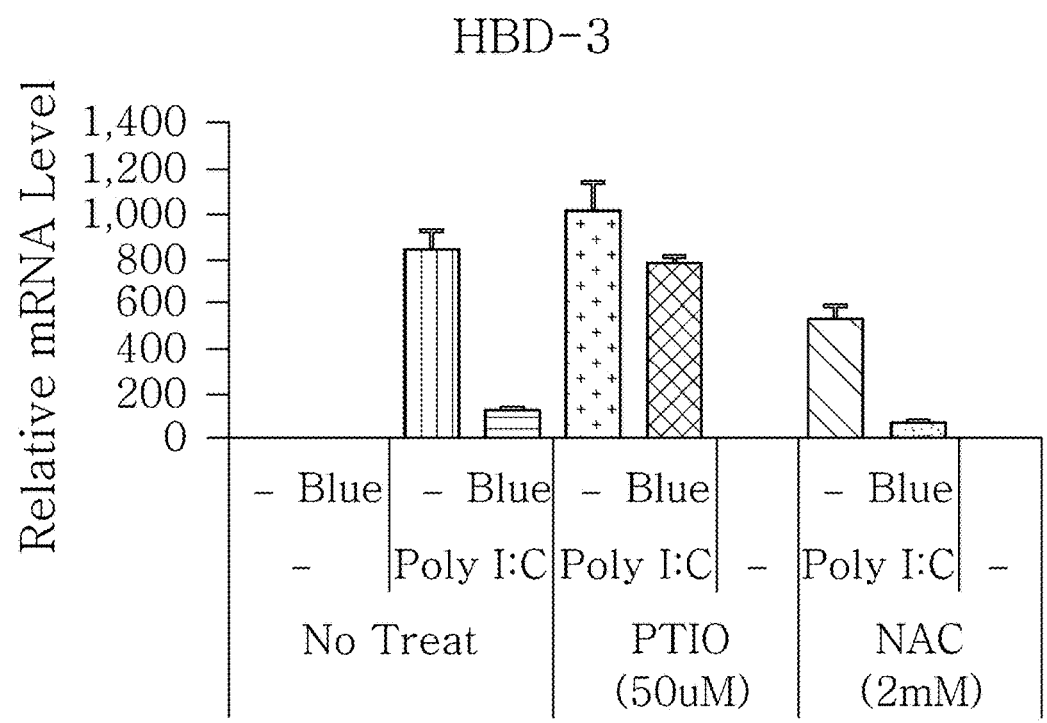

[FIG. 4D]
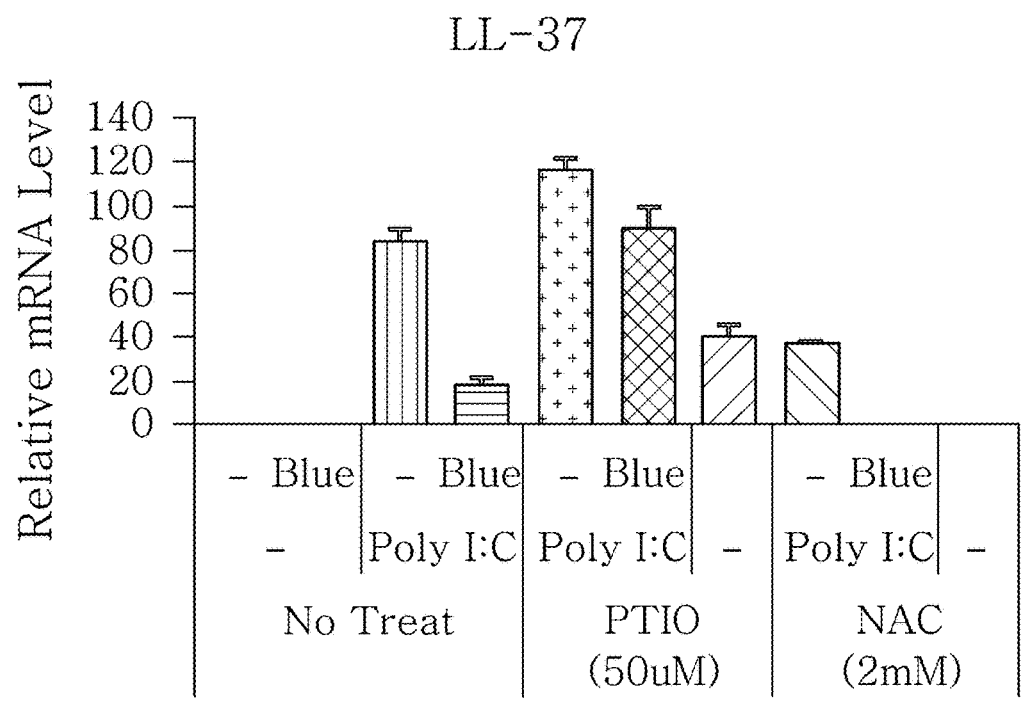

[FIG. 4E]
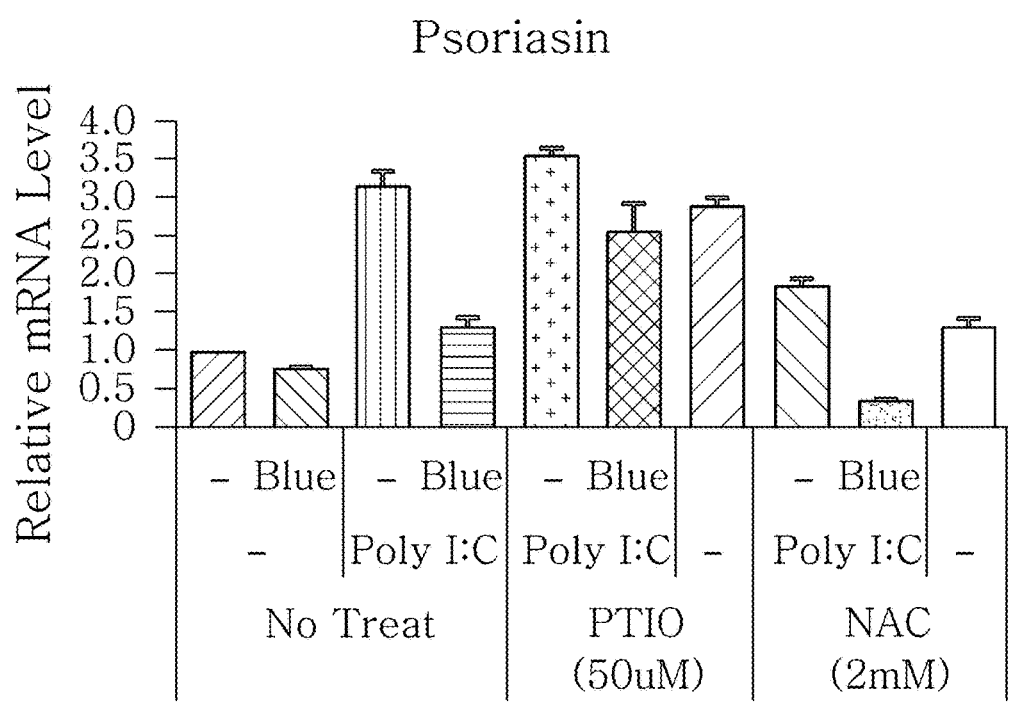

[FIG. 4F]
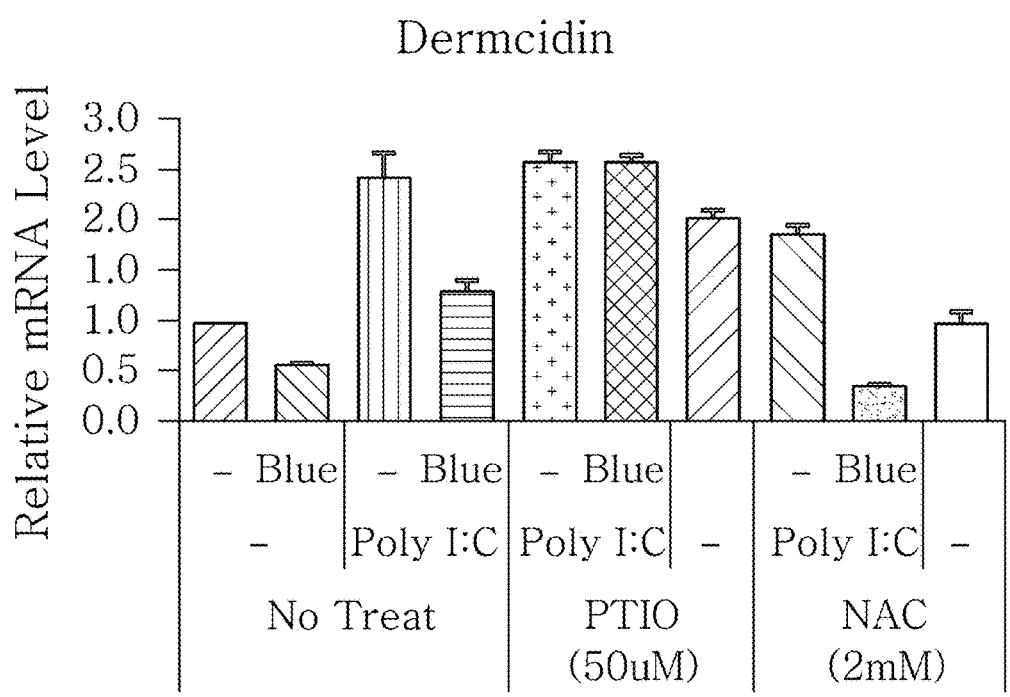

[FIG. 4G]
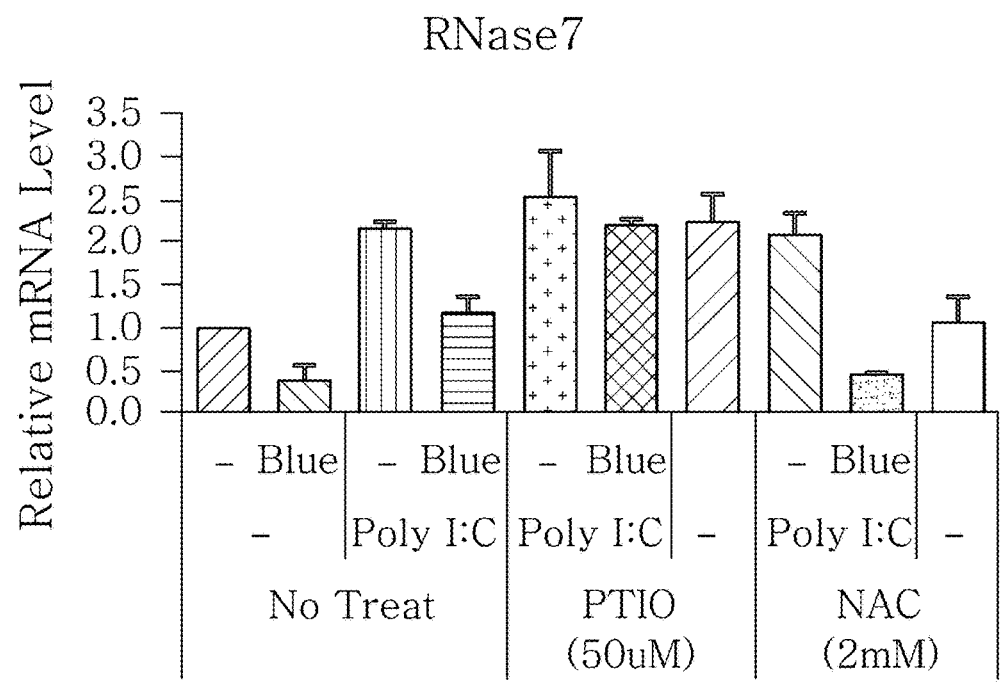

[FIG. 5]
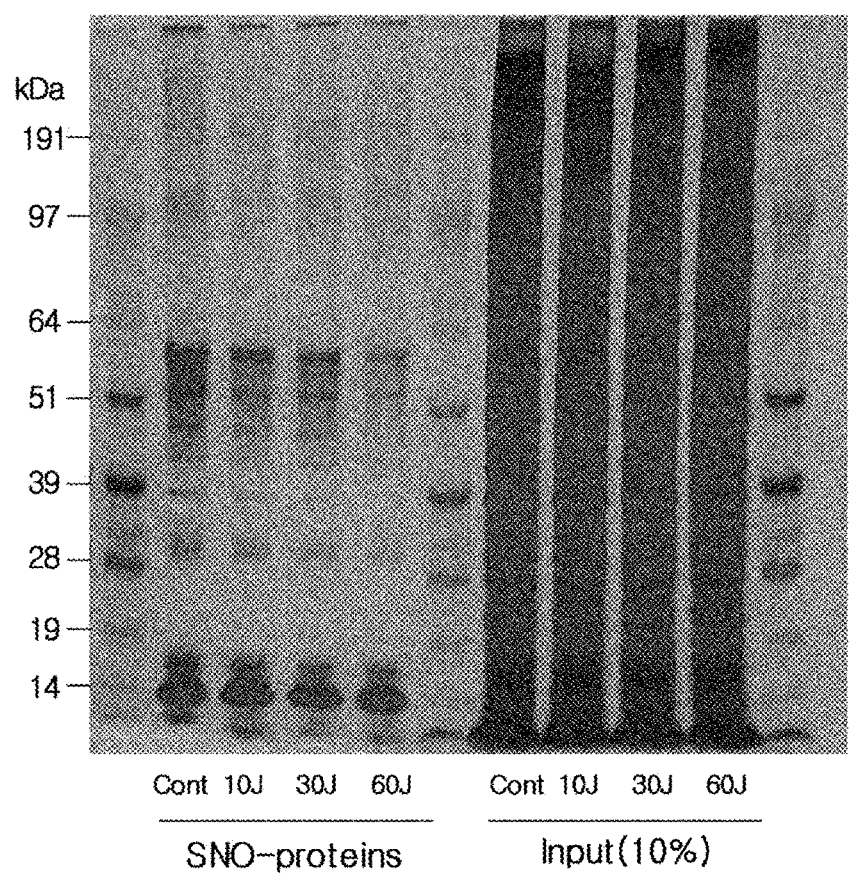

[FIG. 6]
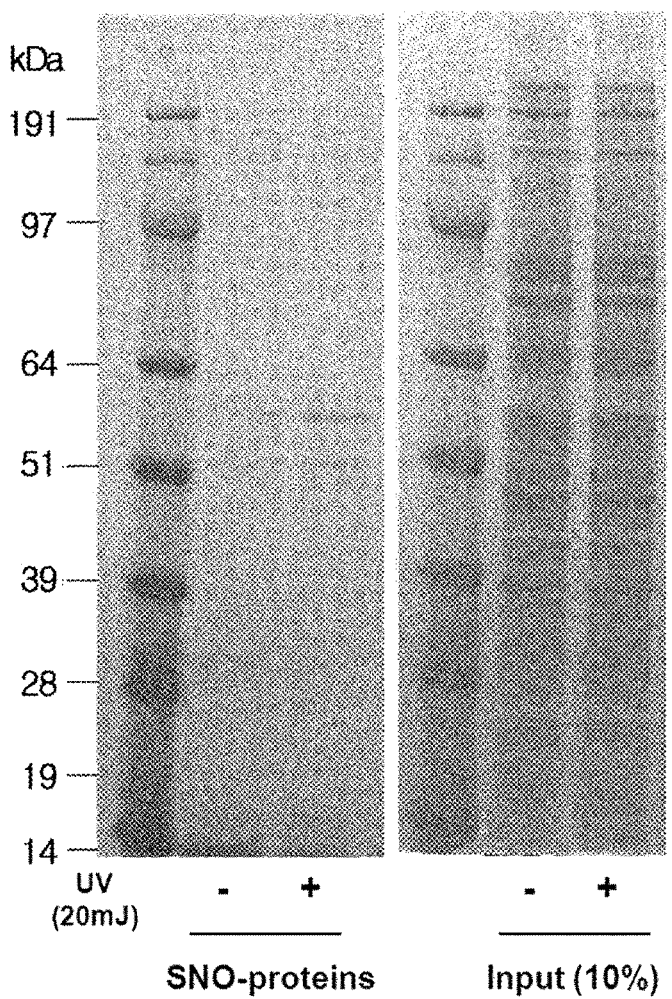

[FIG. 7A]
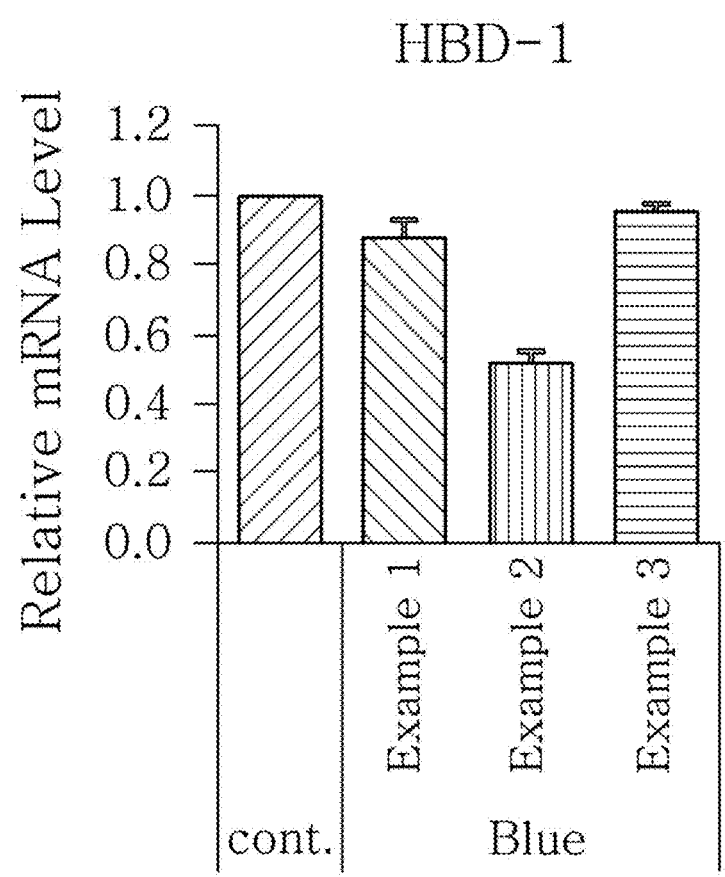

[FIG. 7B]
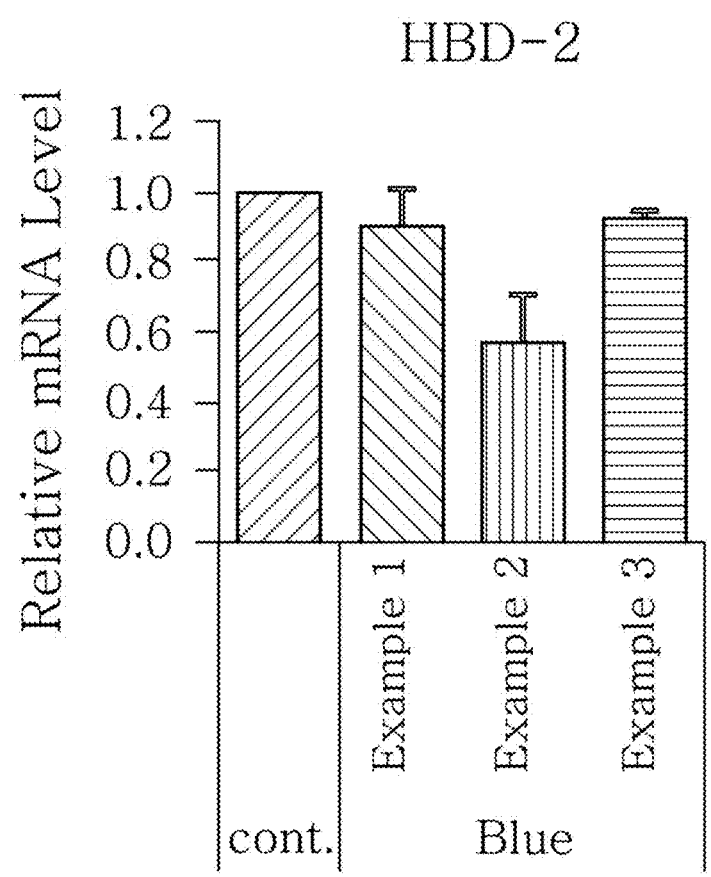

[FIG. 7C]
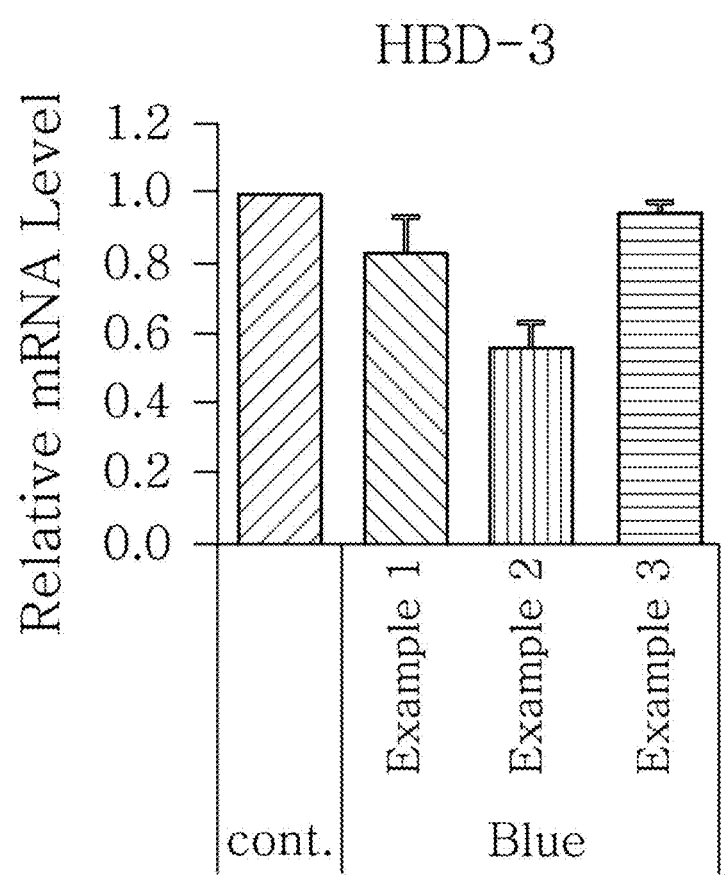

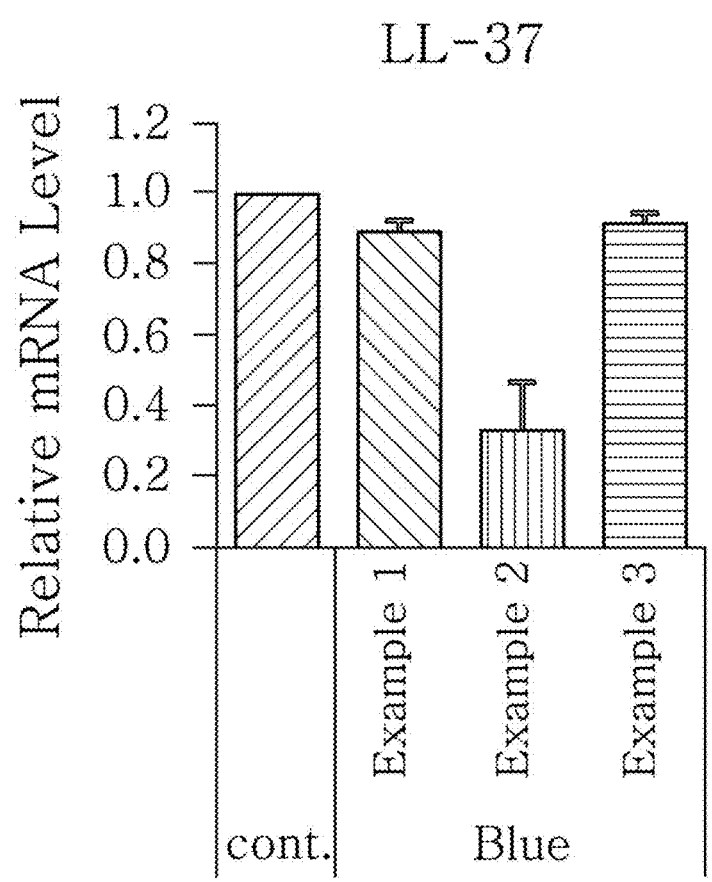
[FIG. 7D]

[FIG. 7E]
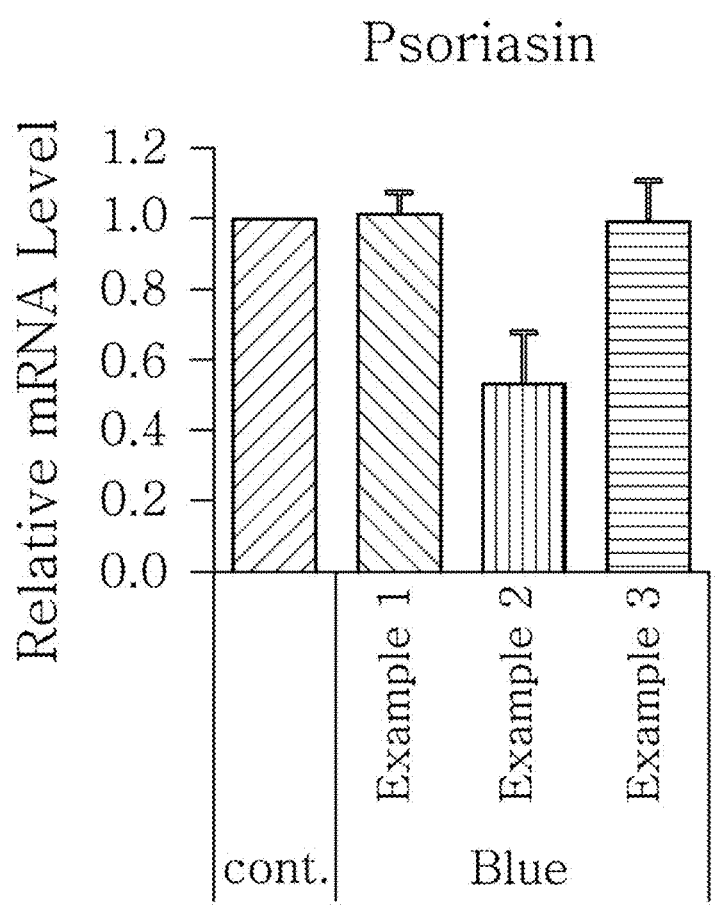

[FIG. 7F]
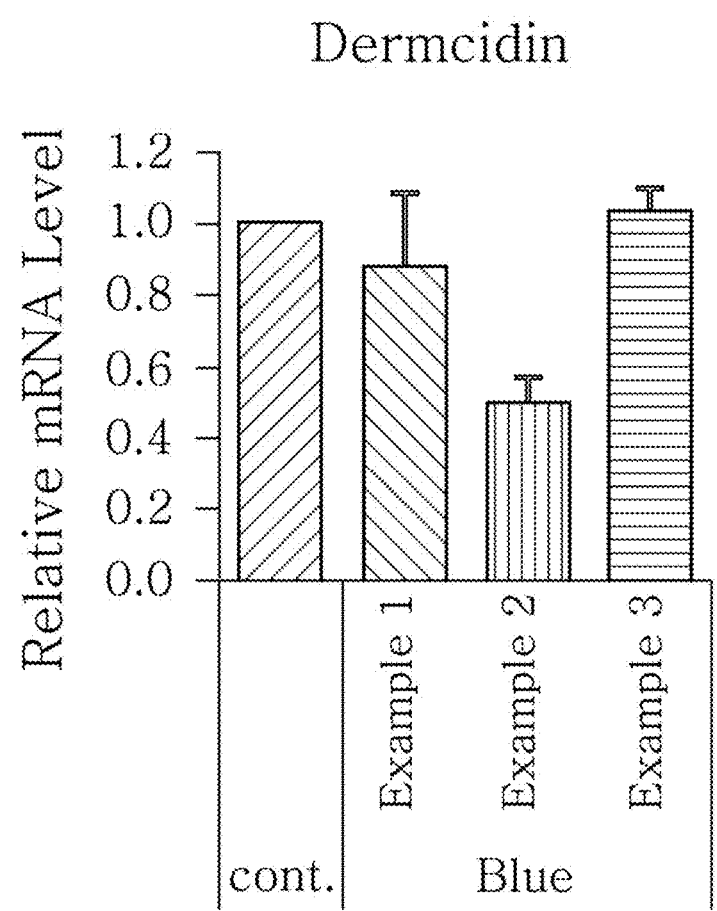

[FIG. 7G]
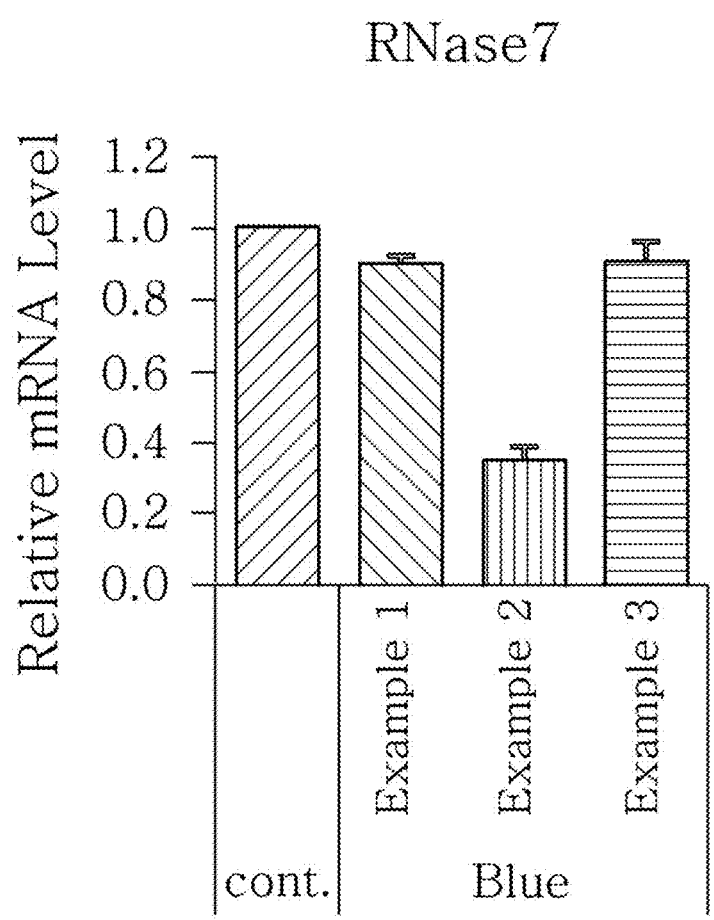

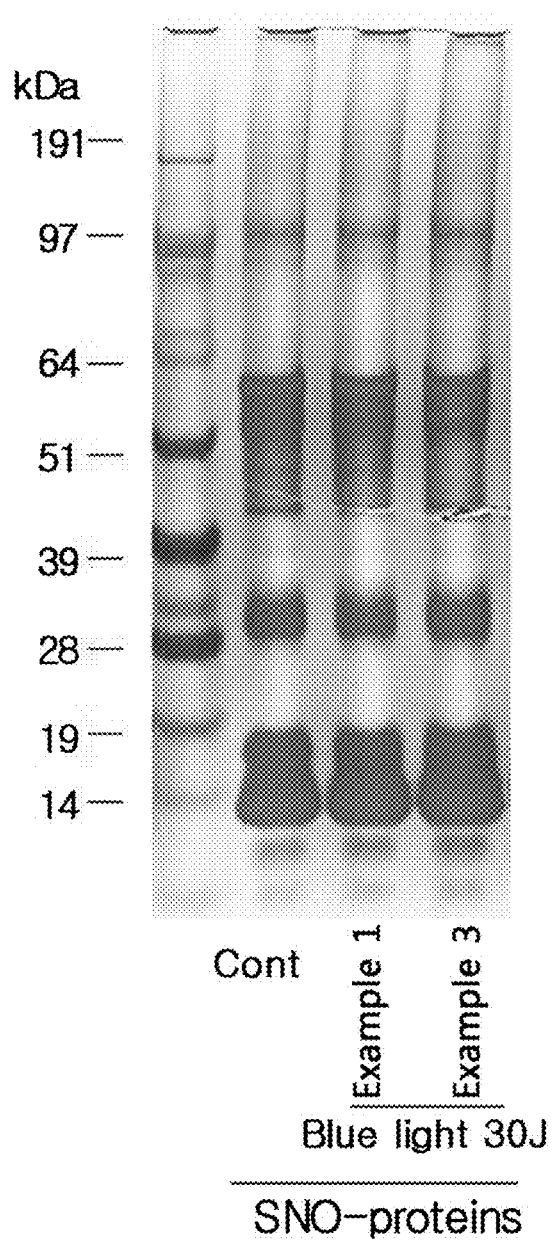
[FIG. 8]

METHOD FOR SCREENING FOR SUNLIGHT PROTECTION FUNCTIONAL MATERIAL AND METHOD FOR EVALUATING SUNLIGHT PROTECTION EFFECT

This application is a U.S. National Stage Application under 35 U.S.C. § 371 of International Patent Application No. PCT/KR2015/002659 filed Mar. 19, 2015, the disclosure of which is hereby incorporated by reference in its entirety. The International Application was published in Korean on Sep. 22, 2016 as WO 2016/148324.

TECHNICAL FIELD

The present invention relates to a method for measuring sunlight protection function through the change of expression of a specific gene in skin cells, specifically to a method for screening sunlight protection functional material or a method for evaluating sunlight protection effect.

BACKGROUND ART

Sunlight (solar energy) consists of radio wave, microwave, infrared ray, visible light, ultraviolet (UV) ray, X-ray, γ-ray, and other in the order of decreasing wavelength. In addition, as the negative effect of sunlight on the skin is known, many products for protecting the skin from sunlight have been developed.

However, although sunlight includes electromagnetic waves of various wavelengths as described above, the sunlight protection effect is mostly determined at present only on the basis of the effectiveness of blocking UV. Accordingly, the effect of sunlight protection products is evaluated in terms of the indices for evaluating UV protection, which are sun protection factor (SPF) representing the erythema caused by the light of UVB range (290-320 nm) and protection of UVA (PA) representing the persistent pigment darkening by the light of UVA range (320-400 nm) through a rater's visual observation. In other words, although UV takes a very small portion in sunlight and electromagnetic waves of other wavelength ranges take a larger portion in sunlight, it is unable to verify the effect of sunlight protection of other wavelengths, except the UV protection effect evaluated in terms of the SPF and PA.

Most of commercially available sunlight protection products have been developed by focusing on the UV protection index, such as SPF and PA. Thus, little research and development works have been performed with regard to sunlight protection of visual light.

In addition, although the sunlight protection products have insufficient function of protecting visual light, including the blue/violet light of a wavelength from 400 to 500 nm which causes skin damage the most in the visual light range, it is unable to verify the effect of blue/violet light protection due to the absence of any protection index enabling the evaluation of the blue/violet light protection effect.

CITATION LIST

Patent Literature

[Patent Literature 1]
Korean Registered Patent: No. 10-0151635.

SUMMARY OF INVENTION

Technical Problem

One aspect of the present invention provides a method for screening sunlight protection functional material by measuring the sunlight protection function, more specifically blue/violet light, or a method for evaluating sunlight protection effect to evaluate the sunlight protection effect. In addition, another aspect of the present invention provides a composition for protecting blue/violet light by the method.

Solution to Problem

To accomplish the purposes, one embodiment of the present invention provides a method for measuring sunlight protection function comprising the step of measuring the change caused by the test material, which is at least one of expression of antimicrobial peptides (AMPs) and production of S-nitrosylated proteins in skin cells, which are reduced by sunlight radiation.

One embodiment of the present invention provides a method for measuring sunlight protection function further comprising the step of screening sunlight protection functional materials, wherein a test material is determined to have a sunlight protection function if the measurement of the change shows inhibition by the test material of the reduction of at least one of expression of AMPs and production of S-nitrosylated proteins in skin cells.

Another embodiment of the present invention provides a method for measuring sunlight protection function further comprising the step of evaluating sunlight protection effect, wherein a test material is determined to have a higher sunlight protection function if the measurement of the change shows greater inhibition by the test material of the reduction of at least one of expression of AMPs and production of S-nitrosylated proteins in skin cells.

In addition, one embodiment of the present invention provides a composition for sunlight protection comprising, as an active ingredient, a material inhibiting the reduction of at least one of expression of AMPs and production of S-nitrosylated proteins in skin cells by blue/violet light of a wavelength from 400 to 500 nm in sunlight.

Advantageous Effects of the Invention

The measurement method of the present invention enables accurate and objective evaluation of sunlight protection, in contrast to the conventional method for evaluating UV protection by visual evaluation, by investigating the reduction of expression of AMPs and production of S-nitrosylated proteins in skin cells by sunlight radiation to the skin, and by using the measurement values as parameters for evaluating sunlight protection function of a test material. The measurement method of the present invention, in contrast to the conventional method for evaluating sunlight protection effect providing only the UV protection index, may determine the protection of blue/violet light in visual light of a wavelength from 400 to 500 nm, which causes skin damage the most, may provide more detailed sunlight protection effect evaluation results, and may prepare an index of sunlight protection degree based on the evaluation results.

In addition, the present invention may provide a composition for protecting even the blue/violet light of a wavelength from 400 to 500 nm by comprising, as an active ingredient, a material determined to have a sunlight protection function by the method described above, in contrast to a conventional composition for UV protection.

BRIEF DESCRIPTION OF DRAWINGS

FIGS. 1a to 1g are plots comparing the change in the expression level (relative mRNA level) of HBD-1, HBD-2, HBD-3, LL-37, psoriasin, dermcidin, and RNase7, which are the AMPS used in one embodiment of the present invention, before (cont.) and after (Blue) blue/violet light radiation.

FIGS. 2a to 2f are plots comparing the change in the respective expression level (relative mRNA level) of HBD-1, HBD-2, HBD-3, psoriasin, dermcidin, and RNase7, which are the AMPS used in one embodiment of the present invention, before (cont.) and after (UV) UV radiation and change depending on radiation intensity.

FIGS. 3a to 3g are plots comparing the change in the respective expression level of HBD-1, HBD-2, HBD-3, LL-37, psoriasin, dermcidin, and RNase7 before (cont.) and after (Blue) blue/violet light radiation when treated with Poly I:C and flagellin to induce viral and bacterial infection situation in human epidermal neonatal keratinocytes.

FIGS. 4a to 4g are plots comparing the change in the respective expression level of HBD-1, HBD-2, HBD-3, LL-37, psoriasin, dermcidin, and RNase7 before (−) and after (Blue) blue/violet light radiation when treated with Poly I:C treatment to induce viral and bacterial infection situation in human epidermal neonatal keratinocyteshuman epidermal neonatal keratinocytes, and also treated with PTIO, a nitric oxide scavenger, and NAC, a reactive oxygen species (ROS) scavenger.

FIG. 5 compares the change (SDS-PAGE gel) in the production of S-nitrosylated (SNO) proteins when blue/violet light is radiated to human epidermal neonatal keratinocytes.

FIG. 6 compares the change (SDS-PAGE gel) in the production of S-nitrosylated (SNO) proteins when UV is radiated to human epidermal neonatal keratinocytes.

FIGS. 7a to 7g are plots comparing the respective expression level of HBD-1, HBD-2, HBD-3, LL-37, psoriasin, dermcidin, and RNase7 in Examples 1 to 3 when blue/violet light is radiated (Blue).

FIG. 8 compares the change (SDS-PAGE gel) in the production of S-nitrosylated (SNO) proteins in Examples 1 to 3 when blue/violet light is radiated.

DESCRIPTION OF EMBODIMENTS

As used herein, the term "sunlight" is the concept with the widest scope incorporating all wavelengths of sunlight, including not only UV but also radio wave, microwave, infrared ray, visible light, X-ray, and γ-ray. In addition, as used herein, the term "skin cell" is the concept with the widest scope incorporating all cells of the tissues covering the body surface of an animal, including not only the tissues covering the body surface at the face and body but also the cells existing in the scalp and hair.

The present invention is described in details hereinafter.

One embodiment of the present invention provides a method for measuring sunlight protection function comprising the step of measuring the change caused by the test material, which is at least one of expression of antimicrobial peptides (AMPs) and production of S-nitrosylated proteins in skin cells, which are reduced by sunlight radiation.

In addition, one embodiment of the present invention provides a method for measuring sunlight protection function further comprising the step of screening sunlight protection functional materials, wherein a test material is determined to have a sunlight protection function if the measurement of the change shows inhibition by the test material of the reduction of at least one of expression of AMPs and production of S-nitrosylated proteins in skin cells.

Another embodiment of the present invention provides a method for measuring sunlight protection function further comprising the step of evaluating sunlight protection effect, wherein a test material is determined to have a higher sunlight protection function if the measurement of the change shows greater inhibition by the test material of the reduction of at least one of expression of AMPs and production of S-nitrosylated proteins in skin cells.

The sunlight radiated in the method for measuring sunlight protection function according to one embodiment of the present invention includes blue/violet light of a wavelength from 400 to 500 nm. In addition, the sunlight may further include UV of a wavelength from 290 to 400 nm.

According to one embodiment of the present invention, the sunlight, specifically blue/violet light of a wavelength from 400 to 500 nm, reduces the expression of the AMPs. In addition, the blue/violet light may reduce the expression level of various cytokines and relevant genes as well as proteins, such as RANTES (Human CCL5), CCL 2 (Chemokine ligand 2), IL-6 (Interleukin-6), IL-8 (Interleukin-8), TNF-α (Tumor necrosis factor-α), and COX-2 (Cyclooxygenase-2).

Specifically, the AMPs are proteins of a small molecular weight having antibiotic activity to prevent infection by pathogens, such as bacteria, virus, and fungi. The AMPs have been reported to induce vascularization, wound healing, and chemotaxis, and have a structural characteristic of being positively charged and having both a hydrophilic site and a hydrophobic site. In one embodiment of the present invention, the AMPs may include at least one of HBD-1 (Human beta-defensin-1, ACCESSION NP_005209, VERSION NP_005029.1 GI: 4885181), HBD-2 (Human beta-defensin-2, ACCESSION NP_004933, VERSION NP_004933.1 GI: 4826692), HBD-3 (Human beta-defensin-3, ACCESSION AAG02237, VERSION AAG02237.1 GI: 49931627), LL-37 (Cathelicidin-37, ACCESSION NP_004336, VERSION NP_004336.3 GI: 348041314), psoriasin (ACCESSION AAA60210, VERSION AAA60210.1 GI: 190668), dermcidin (ACCESSION NP_444513, VERSION NP_444513.1 GI: 16751921) and RNase 7 (ACCESSION CAC84458, VERSION CAC84458.1 GI: 40643235).

The HBD (Human beta-defensin)-1, HBD-2, HBD-3, LL (Cathelicidin)-37, psoriasin, dermcidin, and RNase7 used in the method for measuring sunlight protection function according to one embodiment of the present invention exist in the skin, digestive organs, respiratory organs, and ocular conjunctiva as congenital immunologic factors, and kill or inhibit the growth of Gram positive/negative bacteria and fungal virus. These AMPs also exist, in addition to keratinocytes, in the secreted materials from skin sweat glands and sebaceous glands, and are secreted to and deposited on the skin surface through sweat and sebum to contribute to the formation of an antibiotic barrier. In addition, the AMPs is characterized in that their expression increases by UV radiation, in contrast to blue/violet light radiation. The characteristics of the AMP expression to UV radiation are described in Glaser R. et al. UV-B radiation induces the expression of antimicrobial peptides in human keratinocytes in vitro and in vivo, and J Allergy Clin Immunol. 2009 May; 123(5):1117-23. The entire document is integrated to the present specification as a reference.

Although the expression level of S-nitrosylated proteins increases by UV radiation, according to another embodiment of the present invention, sunlight, specifically blue/violet light of a wavelength from 400 to 500 nm, reduces the production of S-nitrosylated proteins. Specifically, nitric oxide, which is related to many functions in the body, may react with an active cysteine residue to produce S-nitrosylated proteins, and S-nitrosylated proteins may control cellular signal transduction, such as protein activity, like protein phosphorylation. In addition, the blue/violet light may induce de-nitrosylation to detach nitric oxide from an S-nitrosylated protein normally produced in the body through nitrosylation. In addition, when the production of S-nitrosylated proteins decreases by blue/violet light, AMPs may also decrease.

The expression level of the AMP genes or the S-nitrosylated proteins may be measured by a method selected from the group comprising, for example, real time-polymerase chain reaction (RT-PCR), northern blot, enzyme-linked immunosorbent assay (ELISA), radioimmunoassay (RIA), sandwich assay, western blot, immuneblot, immunohistochemical staining, biotin-switch assay, and a combination thereof.

In addition, a method according to one embodiment of the present invention may further comprise the following steps carried out before the measurement of the change: coating a test material on a sunlight transmitting material; placing skin cells below the sunlight transmitting material and then irradiating sunlight on top of the sunlight transmitting material.

The sunlight transmitting material may be any materials transmitting the UV or blue/violet light and having a property which allows coating of a measurement test material. For example, quartz plate or a band pass filter transmitting only a test light band may be used, but not limited thereto. Here, the test material is a material of which sunlight protection effect is to be evaluated and may be any materials applied to human skin, including all products including the material regardless of the formulation, such as cosmetics, drugs, and fibers.

The skin cell used in the method for measuring sunlight protection function according to one embodiment of the present invention may be any human or animal-derived skin cells. For example, at least one of keratinocyte, fibroblast, and melanocyte such as Merkel cell may be used, but not limited thereto.

When the expression level of the AMPs and/or the production of S-nitrosylated proteins in skin cells decreases, the skin immunity decreases. This causes various skin troubles and diseases, and is not good for skin care since it leads to lowered skin moisturizing ability and accelerated skin aging. However, the method for measuring sunlight protection function of the present invention may screen and develop a sunlight protection functional material that may protect blue/violet light, and may prevent the negative effects induced by blue/violet light. According to the present invention, since objective evaluation of the degree of blue/violet light protection effect is possible, it is also possible to index the degree. Furthermore, the method for screening and evaluating effect according to the present invention may be used to discover useful materials in protecting blue/violet light, when these materials are applied to skin, the reduction of AMPs is blocked and there the decrease of natural immunity is blocked and immunity may be increased.

In addition, another embodiment of the present invention may provide a composition for sunlight protection to prevent the reduction of AMPs by blue/violet light, comprising an active ingredient for protecting blue/violet light of a wavelength from 400 to 500 nm, specifically, comprising a material inhibiting the change of at least one of expression level of AMPs and production of S-nitrosylated proteins in skin cells by blue/violet light as an active ingredient. Specifically, the AMPs may be at least one of HBD (Human beta-defensin)-1, HBD-2, HBD-3, LL(Cathelicidin)-37, psoriasin, dermcidin, and RNase 7. The active ingredient of the composition may be a test material of which sunlight protection function is measured by the method for measuring sunlight protection function according to the embodiments of the present invention. The active ingredient may include, for example, at least one of titanium oxide ($TiO_2$), zinc oxide (ZnO), and tinosorb, and any sunlight protection composition included in a sun-screen product.

Hereinafter, the configuration and effect of the present invention will be described in further detail with reference to experimental examples, examples, and comparative examples. It will be obvious that these experimental example, examples, and comparative examples are illustrative purposes only and are not to be construed to limit the category and the scope of the present invention.

Experimental Example 1

As one embodiment of the present invention, an experiment for measuring the change of expression level of AMPs when blue/violet light of a wavelength from 400 to 500 nm is radiated to skin cells was conducted as described below.

First, the human epidermal neonatal keratinocytes used in the present invention were purchased from Lonza, Inc. (Walkersville, Md., US) according to a commercially secured and recommended method. They were subcultured, and then cultured in a $CO_2$ incubator under the conditions of 37° C. and 5% $CO_2$. The culture medium was prepared according to the guideline provided by Lonza, Inc. KGM-2 Bullet kit: BPE (Bovine pituitary extract) 2 ml, hEGF (human epidermal growth factor) 0.5 ml, insulin 0.5 ml, hydrocortisone 0.5 ml, transferrin 0.5 ml, epinephrine 0.5 ml, and gentamycin sulfate+amphotericin-B(GA-1000) 0.5 ml were added to 500 ml of KBM-2 (Clonetics CC-3103) medium.

Subsequently, blue/violet light of a wavelength from 400 to 500 nm was radiated to the medium in which human epidermal neonatal keratinocytes is cultured (10 $J/cm^2$). Then, after removing the culture medium of human epidermal neonatal keratinocytes, the cells were washed with 2 ml of phosphate buffered saline (PBS), and the RNA in the cells were separated by using Trizol reagent (Invitrogen, Carlsbad, Calif., USA).

The separated RNA was once again purified by using an RNA kit (QIAGEN RNeasy kt, QIAGEN, Valencia, Calif.), and then the quality of the RNA was examined by using Agilent 2100 BioAnalyzer (Agilent Technologies, Santa Clara, Calif., USA). The Superscript Reverse Transcriptase (RT) kit (Invitrogen, Carlsbad, Calif.) was used to synthesize cDNA from the RNA, and the cDNA was quantitatively analyzed through a real time-reverse transcription polymerase chain reaction (Q-RT-PCR).

FIGS. 1a to 1g show the results of RT-PCR evaluation of the change of skin genes induced by blue/violet light in the respective expression patterns of HBD-1, HBD-2, HBD-3, LL-37, psoriasin, dermcidin, and RNase 7 by using the TaqMan® gene expression assay kit (Applied Biosystems, Foster City, Calif.). The primers used for the amplification of individual genes in shown in Table 1 below.

TABLE 1

| Name of gene | Primer |
|---|---|
| HBD-1 | Hs00608345_m1 |
| HBD-2 | Hs00175474_m1 |

TABLE 1-continued

| Name of gene | Primer |
| --- | --- |
| HBD-3 | Hs00218678_m1 |
| LL-37 | Hs00189038_m1 |
| Psoriasin | Hs00161488_m1 |
| Dermcidin | Hs00364976_m1 |
| RNase7 | Hs00922963_s1 |

The results, as shown in FIGS. 1a to 1g, show that the respective expression level (relative mRNA level) of the congenital immunity genes (i.e. AMPs), HBD-1, HBD-2, HBD-3, LL-37, psoriasin, dermcidin, and RNase7, was reduced after (Blue) blue/violet light radiation in comparison with the level before (cont.) the radiation. This is in contrast to the result of the experiment performed under the same conditions as described above, except that UV (10, 30 mJ) was radiated instead of blue/violet light, wherein, when UV is radiated, the expression level of the in vivo HBD-1, HBD-2, HBD-3, LL-37, psoriasin, dermcidin, and RNase7 increased as the radiation intensity increased (see FIGS. 2a to 2f.). This indicates that the effect of sunlight on the skin is dependent on the wavelength, and the expression level of the AMPs may be used as an index for measuring the blue/violet light protection function and for evaluating the effect.

Experimental Example 2

As one embodiment of the present invention, an experiment for measuring the change of expression level of AMPs when blue/violet light of a wavelength from 400 to 500 nm is radiated to skin cells was conducted as described below.

First, according to a commercially secured and recommended method, the human epidermal neonatal keratinocytes used in the present invention were purchased from Lonza, Inc. (Walkersville, Md., US), subcultured, and then cultured in a $CO_2$ incubator under the conditions of 37° C. and 5% $CO_2$. The culture medium was prepared according to the guideline provided by Lonza, Inc. KGM-2 Bullet kit: BPE (Bovine pituitary extract) 2 ml, hEGF (human epidermal growth factor) 0.5 ml, insulin 0.5 ml, hydrocortisone 0.5 ml, transferrin 0.5 ml, epinephrine 0.5 ml, and gentamycin sulfate+amphotericin-B(GA-1000) 0.5 ml were added to 500 ml of KBM-2 (Clonetics CC-3103) medium.

Subsequently, blue/violet light of a wavelength from 400 to 500 nm was radiated to the medium in which human epidermal neonatal keratinocytes is cultured (10 $J/cm^2$). Then, after removing the culture medium of human epidermal neonatal keratinocytes, the cells were washed with 2 ml of phosphate buffered saline (PBS), and the RNA in the cells were separated by using Trizol reagent (Invitrogen, Carlsbad, Calif., USA).

At this time, Poly I:C and flagellin (Invivogen, San Diego, Calif., USA) treatment was performed to induce viral and bacterial infection situation before and after the radiation of the blue/violet light (10 $J/cm^2$).

Then, the separated RNA was once again purified by using an RNA kit (QIAGEN RNeasy kt, QIAGEN, Valencia, Calif.), and then the quality of the RNA was examined by using Agilent 2100 BioAnalyzer (Agilent Technologies, Santa Clara, Calif., USA). The Superscript Reverse Transcriptase (RT) kit (Invitrogen, Carlsbad, Calif.) was used to synthesize cDNA from the RNA, and the cDNA was quantitatively analyzed through a real time-reverse transcription polymerase chain reaction (Q-RT-PCR).

FIGS. 3a to 3g show the results of RT-PCR evaluation of the change of skin genes induced by blue/violet light in the expression patterns of HBD-1, HBD-2, HBD-3, LL-37, psoriasin, dermcidin, and RNase 7 by using the TaqMan® gene expression assay kit (Applied Biosystems, Foster City, Calif.). The primers used for the amplification of individual genes is shown in table 1.

FIGS. 3a to 3g are plots comparing the change in the respective expression level of HBD-1, HBD-2, HBD-3, LL-37, psoriasin, dermcidin, and RNase7 before (cont.) and after (Blue) blue/violet light radiation when treated with Poly I:C and flagellin treatment to induce viral and bacterial infection situation in human epidermal neonatal keratinocytes. As shown in FIG. 3, the expression level of the respective genes was reduced by the radiation of blue/violet light, when HBD-1, HBD-2, HBD-3, LL-37, psoriasin, dermcidin, and RNase7 were increased by Poly I:C and flagellin treatment. The increase and decrease were statistically significant. The statistics were verified by two-tailed Student's t-test, and it is considered to be significantly different when a p-value is 0.05 or less. This indicates that the expression level of AMPs may be used as an index for measuring the blue/violet light protection function and for evaluating the effect.

Experimental Example 3

As one embodiment of the present invention, an experiment for measuring the change of expression level of AMPs when blue/violet light of a wavelength from 400 to 500 nm is radiated to skin cells was conducted as described below.

First, according to a commercially secured and recommended method, the human epidermal neonatal keratinocytes used in the present invention were purchased from Lonza, Inc. (Walkersville, Md., US), subcultured, and then cultured in a $CO_2$ incubator under the conditions of 37° C. and 5% $CO_2$. The culture medium was prepared according to the guideline provided by Lonza, Inc. KGM-2 Bullet kit: BPE (Bovine pituitary extract) 2 ml, hEGF (human epidermal growth factor) 0.5 ml, insulin 0.5 ml, hydrocortisone 0.5 ml, transferrin 0.5 ml, epinephrine 0.5 ml, and gentamycin sulfate+amphotericin-B(GA-1000) 0.5 ml were added to 500 ml of KBM-2 (Clonetics CC-3103) medium.

Subsequently, blue/violet light of a wavelength from 400 to 500 nm was radiated to the medium in which human epidermal neonatal keratinocytes is cultured (10 $J/cm^2$). Then, after removing the culture medium of human epidermal neonatal keratinocytes, the cells were washed with 2 ml of phosphate buffered saline (PBS), and the RNA in the cells were separated by using Trizol reagent (Invitrogen, Carlsbad, Calif., USA).

At that time, Poly I:C treatment was performed to induce viral and bacterial infection situation before and after the radiation of the blue/violet light (10 $J/cm^2$). In addition, the RNA was treated with PTIO (2-(4-Carboxyphenyl)-4,4,5,5-tetramethylimidazoline-1-oxyl-3-oxide potassium salt), a nitric oxide scavenger, and NAC (N-Acetyl-L-cysteine) (Sigma, St. Louis, Mo., USA), a ROS scavenger, respectively.

Then, the separated RNA was once again purified by using an RNA kit (QIAGEN RNeasy kt, QIAGEN, Valencia, Calif.), and then the quality of the RNA was examined by using Agilent 2100 BioAnalyzer (Agilent Technologies, Santa Clara, Calif., USA). The Superscript Reverse Transcriptase (RT) kit (Invitrogen, Carlsbad, Calif.) was used to synthesize cDNA from the RNA, and the cDNA was quantitatively analyzed through a real time-reverse transcription polymerase chain reaction (Q-RT-PCR).

FIGS. 4a to 4g show the results of RT-PCR evaluation of the change of skin genes induced by blue/violet light in the expression patterns of HBD-1, HBD-2, HBD-3, LL-37, psoriasin, dermcidin, and RNase 7 by using the TaqMan® gene expression assay kit (Applied Biosystems, Foster City, Calif.). The primers used for the amplification of individual genes is shown in table 1.

The results, as shown in FIGS. 4a to 4g, show that the expression level of HBD-1, HBD-2, HBD-3, LL-37, psoriasin, dermcidin, and RNase 7 increased by the Poly I:C treatment was reduced by the blue/violet light radiation, and that the expression level of the AMPs was not reduced even by the blue/violet light radiation in the group treated with PTIO, a nitric oxide scavenger, among the two scavengers used for treatment. This indicates that blue/violet light is involved in the production of S-nitrosylated proteins and the regulation of the expression level of AMPs.

Experimental Example 4

As one embodiment of the present invention, an experiment for measuring the change of production of S-nitrosylated proteins when blue/violet light of a wavelength from 400 to 500 nm is radiated to skin cells was performed as described below.

First, according to a commercially secured and recommended method, the human epidermal neonatal keratinocytes used in the present invention were purchased from Lonza, Inc. (Walkersville, Md., US), subcultured, and then cultured in a $CO_2$ incubator under the conditions of 37° C. and 5% $CO_2$. The culture medium was prepared according to the guideline provided by Lonza, Inc. KGM-2 Bullet kit: BPE (Bovine pituitary extract) 2 ml, hEGF (human epidermal growth factor) 0.5 ml, insulin 0.5 ml, hydrocortisone 0.5 ml, transferrin 0.5 ml, epinephrine 0.5 ml, and gentamycin sulfate+amphotericin-B(GA-1000) 0.5 ml were added to 500 ml of KBM-2 (Clonetics CC-3103) medium.

After radiating blue/violet light of a wavelength from 400 to 500 nm at 10, 30, and 60 $J/cm^2$ to the cultured cells, the culture medium of human epidermal neonatal keratinocytes was removed and the cells were washed with 2 ml of phosphate buffered saline (PBS). Then a biotin-switch assay was performed to detect the production of S-nitrosylated proteins. Specifically, the washed cells were lysed in HENTS solution (HEPES, Triton X100, SDS, protease inhibitor, EDTA) for 10 minutes, and only the supernatant was taken. After quantifying the proteins, the concentration was adjusted to 600 ug/200 ul by using HEN solution (HEPES, protease inhibitor, EDTA). To prevent the reaction of cysteine that was not S-nitrosylated, MMTS (Sigma) was added to the concentration of 10 mM, and then a reaction was performed at 50° C. for 15 minutes. After precipitating the proteins with acetone, the proteins were dissolved in a 50 mM ascorbic acid (Sigma) HENS solution (HEPES, SDS, protease inhibitor, EDTA) containing 1 mM HPDP-biotin (Pierce) and then underwent a reaction at 37° C. for one hour to conjugate biotin the S-nitrosylated cysteine. After precipitating the proteins with acetone, the proteins were dissolved in a HENS solution. After 5% of the input was separated for calibration, avidin-agarose beads (Pierce) were added by 20 μl each, and underwent a reaction at 4° C. for 12 hours. The beads were washed five times with a neutralization solution (HEPES, EDTA, NaCl, Triton X 100), and then a sample buffer was added. The resulting mixture was boiled and then underwent SDS-PAGE with the input. Subsequently, the S-nitrosylated proteins were identified with SDS-PAGE through silver staining. The result is shown in FIG. 5.

The results, as shown in FIG. 5, in comparison with the control sample (cont) that did not undergo blue/violet light radiation, show that the production of in vivo S-nitrosylated proteins (SNO-proteins) decreased as the intensity of the blue/violet light radiation increased.

This is in contrast to the result of the experiment performed under the same conditions as described above, except UV (20 mJ) was radiated instead of blue/violet light, wherein, when UV is radiated, the production of S-nitrosylated proteins (SNO-proteins) increased (See FIG. 6). This indicates that the effect of sunlight on the skin is dependent on the wavelength, and the production of S-nitrosylated proteins may be used as an index for measuring the blue/violet light protection function and for evaluating the effect.

Experimental Example 5

According to one embodiment of the present invention, before measuring the sunlight protection function for skin cells of a test material, UV and blue/violet light transmittance of a test material was measured by the method described below.

Before the experiment, sunlight protection formulations of Examples 1 to 3 were prepared as test materials in the compositions shown below by a method commonly used in the art (Unit: wt %).

TABLE 2

| Composition | Example 1 | Example 2 | Example 3 |
|---|---|---|---|
| $TiO_2$ | 2 | 2 | 2 |
| ZnO | 2 | 2 | 2 |
| OMC(octyl methoxy cinnamate) | 7 | 7 | 7 |
| Ethylhexyl Salicylate (Ethylhexyl Salicylate) | — | 3 | 3 |
| Tinosorb S | 3 | — | 3 |
| Cetiol CC | 5.00 | 5.00 | 5.00 |
| Nomcort-HK-G | 1.50 | 1.50 | 1.50 |
| Ozokerite | 1.00 | 1.00 | 1.00 |
| Abil EM90 | 1.50 | 1.50 | 1.50 |
| Crill-6 | 0.50 | 0.50 | 0.50 |
| Bentone 27VCG | 1.40 | 1.40 | 1.40 |
| DC 2-9040 | 3.00 | 3.00 | 3.00 |
| DC 345 | 3.00 | 3.00 | 3.00 |
| Finsolv TN | 20.00 | 20.00 | 20.00 |
| Distilled water | 42.73 | 42.73 | 39.73 |
| EDTA.2Na | 0.02 | 0.02 | 0.02 |
| NaCl | 1.00 | 1.00 | 1.00 |
| Glycerin | 5.00 | 5.00 | 5.00 |
| Polyethylene (PE) | 0.30 | 0.30 | 0.30 |
| Sensiva SC50 | 0.05 | 0.05 | 0.05 |
| Total | 100.00 | 100.00 | 100.00 |

Then, the clinical SPF and PA values, and the blue/violet light transmittance of Examples 1 to 3 were measured, respectively. The results are shown in Table 3. The blue/violet light transmittance was measured by coating 2 $mg/cm^2$ of sunlight protection formulations of Examples 1 to 3 on band-pass filters, respectively, radiating a light source including the blue/violet light band, and measuring the transmitted blue/violet light band (400-500 nm) with SPF-290S Sunscreen Analyzer System, which is a spectrophotometer. The SPF (erythema) and PA (persistent pigment darkening) by UV verification experiment was performed according to the sunscreen analysis experiment method of Korea Food & Drug Administration (KFDA).

TABLE 3

| Tested materials | SPF | PA | Blue/Violet protection ratio (%) |
|---|---|---|---|
| Example 1 | 30 | +++ | 51.3% |
| Example 2 | 30 | ++ | 15.4% |
| Example 3 | 30 | +++ | 56.4% |

Table 3 shows that the sunlight protection formulations of Examples 1 to 3 had almost the same SPF and PA values against UV, but significantly different transmittance of blue/violet light. This indicates that sunlight protection products having the same UV protection effect may have a different effect of protecting blue/violet light of a wavelength from 400 to 500 nm in visible light. Therefore, the SPF and PA values may not comprehensively represent the presence of overall sunlight protection function or the degree of sunlight protection effect.

Experimental Example 6

As one embodiment of the present invention, an experiment for measuring the change of expression level of AMPs when blue/violet light with a wavelength from 400 to 500 nm is radiated to skin cells depending on the materials having the sunlight protection function was performed as described below.

First, according to a commercially secured and recommended method, the human epidermal neonatal keratinocytes used in the present invention were purchased from Lonza, Inc. (Walkersville, Md., US), subcultured, and then cultured in a $CO_2$ incubator under the conditions of 37° C. and 5% $CO_2$. The culture medium was prepared according to the guideline provided by Lonza, Inc. KGM-2 Bullet kit: BPE (Bovine pituitary extract) 2 ml, hEGF (human epidermal growth factor) 0.5 ml, insulin 0.5 ml, hydrocortisone 0.5 ml, transferrin 0.5 ml, epinephrine 0.5 ml, and gentamycin sulfate+amphotericin-B(GA-1000) 0.5 ml were added to 500 ml of KBM-2 (Clonetics CC-3103) medium.

Then, 2 mg/cm$^2$ of the sunlight protection formulations of Examples 1 to 3 used in Experimental Example 5 was coated on band-pass filters, below which human epidermal neonatal keratinocytes were placed. Then, blue/violet light of wavelength from 400 to 500 nm was radiated over the regions coated with the sunlight protection formulations at the intensity of 0 and 30 J/cm$^2$. Then, after removing the culture medium of human epidermal neonatal keratinocytes, the cells were washed with 2 ml of phosphate buffered saline (PBS), and the RNA in the cells were separated by using Trizol reagent (Invitrogen, Carlsbad, Calif., USA).

The separated RNA was once again purified by using an RNA kit (QIAGEN RNeasy kt, QIAGEN, Valencia, Calif.), and then the quality of the RNA was examined by using Agilent 2100 BioAnalyzer (Agilent Technologies, Santa Clara, Calif., USA). The Superscript Reverse Transcriptase (RT) kit (Invitrogen, Carlsbad, Calif.) was used to synthesize cDNA from the RNA, and the cDNA was quantitatively analyzed through a real time-reverse transcription polymerase chain reaction (Q-RT-PCR).

FIG. 7 shows the results of RT-PCR evaluation of the change of skin genes induced by blue/violet light in the expression patterns of HBD-1, HBD-2, HBD-3, LL-37, psoriasin, dermcidin, and RNase 7 by using the TaqMan® gene expression assay kit (Applied Biosystems, Foster City, Calif.). The primers used for the amplification of individual genes is shown in table 1.

The results, as shown in FIGS. 7a to 7g, show that when blue/violet light is radiated, the expression level of HBD-1, HBD-2, HBD-3, LL-37, psoriasin, dermcidin, and RNase 7 was reduced in Examples 1 to 3, but the degree of reduction was dependent on the blue/violet light protection effect of Examples 1 to 3. This indicates that the expression level of AMPs may be used as an index for evaluating the blue/violet light protection function.

Experimental Example 7

As one embodiment of the present invention, an experiment for measuring the change of the production of S-nitrosylated proteins when blue/violet light of a wavelength from 400 to 500 nm is radiated to skin cells depending on the materials having the sunlight protection function was performed as described below.

First, the human epidermal neonatal keratinocytes used in the present invention were purchased from Lonza, Inc. (Walkersville, Md., US) according to a commercially secured and recommended method. They were subcultured, and then cultured in a $CO_2$ incubator under the conditions of 37° C. and 5% $CO_2$. The culture medium was prepared according to the guideline provided by Lonza, Inc. KGM-2 Bullet kit: BPE (Bovine pituitary extract) 2 ml, hEGF (human epidermal growth factor) 0.5 ml, insulin 0.5 ml, hydrocortisone 0.5 ml, transferrin 0.5 ml, epinephrine 0.5 ml, and gentamycin sulfate+amphotericin-B(GA-1000) 0.5 ml were added to 500 ml of KBM-2 (Clonetics CC-3103) medium.

Then, 2 mg/cm$^2$ of the sunlight protection formulations of Examples 1 to 3 used in Experimental Example 4 was coated on band-pass filters, below which human epidermal neonatal keratinocytes were placed. Then blue/violet light of a wavelength from 400 to 500 nm was radiated over the regions coated with the sunlight protection formulations at the intensity of 30 J/cm$^2$.

Next, the culture medium of human epidermal neonatal keratinocytes was removed and the cells were washed with 2 ml of phosphate buffered saline (PBS). Then a biotin-switch assay was performed to detect the production of S-nitrosylated proteins. Specifically, the washed cells were lysed in HENTS solution (HEPES, Triton X100, SDS, protease inhibitor, EDTA) for 10 minutes, and only the supernatant was taken. After quantifying the proteins, the concentration was adjusted to 600 µg/200 µl by using HEN solution (HEPES, protease inhibitor, EDTA). To prevent the reaction of cysteine that was not S-nitrosylated, MMTS (Sigma) was added to the concentration of 10 mM, and then a reaction was performed at 50° C. for 15 minutes. After precipitating the proteins with acetone, the proteins were dissolved in a 50 mM ascorbic acid (Sigma) HENS solution (HEPES, SDS, protease inhibitor, EDTA) containing 1 mM HPDP-biotin (Pierce) and then underwent a reaction at 37° C. for one hour to conjugate biotin the S-nitrosylated cysteine. After precipitating the proteins with acetone, the proteins were dissolved in a HENS solution. After 5% of the input was separated for calibration, avidin-agarose beads (Pierce) were added by 20 µl each, and underwent a reaction at 4° C. for 12 hours. The beads were washed five times with a neutralization solution (HEPES, EDTA, NaCl, Triton X 100), and then a sample buffer was added. The resulting mixture was boiled and then underwent SDS-PAGE with the input. Subsequently, the S-nitrosylated proteins were identified with SDS-PAGE through silver staining. The result of the SDS-PAGE is shown in FIG. 8.

The results, as shown in FIG. 8, in comparison with the control sample (cont) that did not undergo blue/violet light radiation, show that the production of in vivo S-nitrosylated proteins (SNO-proteins) was dependent on the sunlight protection effect of Examples 1 to 3. This indicates that the production of S-nitrosylated proteins may be used as an index for evaluating the blue/violet light protection function.

The invention claimed is:

1. A method for measuring sunlight protection function comprising the step of measuring the change caused by a test material in at least one of expression of antimicrobial peptides (AMPs) and production of S-nitrosylated proteins in skin cells after irradiating sunlight in comparison with the skin cells before irradiating sunlight, which are reduced by sunlight radiation,
   wherein the method further comprises the following steps carried out before the measurement of the change;
   coating the test material on a sunlight transmitting material; and
   placing skin cells below the sunlight transmitting material and then irradiating sunlight on top of the sunlight transmitting material, and
   wherein the sunlight is blue/violet light of a wavelength from 400 to 500 nm, and the AMP is at least one of HBD (Human beta-defensin)-1, HBD-2, HBD-3, LL (Cathelicidin)-37, psoriasin, dermcidin, and RNase 7.

2. The method for measuring sunlight protection function of claim 1, further comprising the step of screening sunlight protection functional materials, wherein a test material is determined to have a sunlight protection function if the measurement of the change shows inhibition by the test material of the reduction of at least one of expression of AMPS and production of S-nitrosylated proteins in skin cells.

3. The method for measuring sunlight protection function of claim 1, further comprising the step of evaluating sunlight protection effect, wherein a test material is determined to have a higher sunlight protection function if the measurement of the change shows statistically significant greater inhibition by the test material of the reduction of at least one of expression of AMPS and production of S-nitrosylated proteins in skin cells.

4. The method for measuring sunlight protection function of claim 1, wherein the sunlight transmitting material is a quartz plate or a band pass filter.

5. The method for measuring sunlight protection function of claim 1, wherein the skin cell is at least one of keratinocyte, fibroblast, and melanocyte.

* * * * *